(12) United States Patent
Morishita et al.

(10) Patent No.: US 12,185,940 B2
(45) Date of Patent: *Jan. 7, 2025

(54) METHOD FOR CLOSING WOUND

(71) Applicant: OLYMPUS MEDICAL SYSTEMS CORP., Hachioji (JP)

(72) Inventors: Hiroyuki Morishita, Hachioji (JP); Kunihide Kaji, Hachioji (JP); Keita Ozawa, Hino (JP)

(73) Assignee: OLYMPUS MEDICAL SYSTEMS CORP., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 18/379,352

(22) Filed: Oct. 12, 2023

(65) Prior Publication Data

US 2024/0032910 A1 Feb. 1, 2024

Related U.S. Application Data

(63) Continuation of application No. 17/585,135, filed on Jan. 26, 2022, now Pat. No. 11,819,206.

(60) Provisional application No. 63/154,908, filed on Mar. 1, 2021.

(51) Int. Cl.
*A61B 17/04* (2006.01)
*A61B 17/00* (2006.01)

(52) U.S. Cl.
CPC ..... *A61B 17/0469* (2013.01); *A61B 2017/00818* (2013.01)

(58) Field of Classification Search
CPC .................. A61B 17/0469; A61B 2017/00818
See application file for complete search history.

(56) References Cited

U.S. PATENT DOCUMENTS

| 5,364,409 | A | 11/1994 | Kuwabara et al. |
| 5,709,694 | A | 1/1998 | Greenberg et al. |
| 5,792,177 | A | 8/1998 | Kaseda |
| 5,814,054 | A | 9/1998 | Kortenbach et al. |
| 7,731,727 | B2 * | 6/2010 | Sauer ............ A61B 17/320016 606/139 |
| 8,758,375 | B2 | 6/2014 | Mikkaichi et al. |

(Continued)

FOREIGN PATENT DOCUMENTS

| EP | 3 031 402 A1 | 6/2016 |
| WO | 2015/019781 A1 | 2/2015 |

OTHER PUBLICATIONS

Aug. 7, 2023 Notice of Allowance issued in U.S. Appl. No. 17/585,135.

*Primary Examiner* — Ryan J. Severson
(74) *Attorney, Agent, or Firm* — Oliff PLC

(57) ABSTRACT

A method for closing a wound in a tubular organ using a suture thread includes: a first step of connecting a first edge portion and a second edge portion with the suture thread; and a second step of connecting a third edge portion and a fourth edge portion with the suture thread. The first step includes passing the suture thread through a first position on a mucosal surface of at least one of the first edge portion and the second edge portion. The second step includes passing the suture thread through a third position on the mucosal surface of at least one of the third edge portion and the fourth edge portion. A shortest distance between the wound and the third position is larger than a shortest distance between the wound and the first position.

7 Claims, 22 Drawing Sheets

(56) References Cited

U.S. PATENT DOCUMENTS

| | | |
|---|---|---|
| 9,693,769 B2 | 7/2017 | Takahashi et al. |
| 10,905,467 B2 | 2/2021 | Goto |
| 11,819,206 B2 * | 11/2023 | Morishita .......... A61B 17/0469 |
| 2007/0073320 A1 | 3/2007 | Mikkaichi et al. |
| 2007/0255296 A1 | 11/2007 | Sauer |
| 2010/0211082 A1 | 8/2010 | Sauer |
| 2016/0038140 A1 | 2/2016 | Takahashi et al. |
| 2019/0290325 A1 | 9/2019 | Goto |
| 2022/0273286 A1 | 9/2022 | Morishita et al. |
| 2024/0032910 A1 * | 2/2024 | Morishita ............ A61B 17/062 |

* cited by examiner

METHOD FOR CLOSING WOUND

CROSS-REFERENCE TO RELATED APPLICATIONS

This is a Continuation of U.S. patent application Ser. No. 17/585,135 filed Jan. 26, 2022, which in turn claims priority from U.S. Patent Application No. 63/154,908, filed on Mar. 1, 2021. The disclosure of the prior applications is hereby incorporated by reference herein in its entirety.

BACKGROUND

Technical Field

The present disclosure relates to a method for closing a wound.

Background

Conventionally, a technique of transendoscopically closing a part (wound) where the mucosa in a tubular organ such as the digestive tract is defective by ESD (endoscopic submucosal dissection) has been performed. For example, a method is known for closing a portion (wound) in which a mucous membrane is defective under observation with an endoscope by using a suture thread device, a needle holder, a clip device, or the like. A wound closing method that can effectively close the wound even when the mucosal defect (wound) is large is desired.

A known suturing method uses a suture thread device and an endoscope to continuously sutured tissue without taking the suture thread device introduced into the patient's body out of the body. The tissue opening is closed by inserting a suture needle into the edge of the tissue opening and passing the suture thread through the edge.

SUMMARY

A first aspect of the present disclosure is a method for closing a wound in a tubular organ using a suture thread. A peripheral edge of the wound includes a first edge portion, a second edge portion located opposite the first edge portion across the wound, a third edge portion adjacent to the second edge portion, and a fourth edge portion located opposite the third edge portion across the wound. An opening of the wound is largest between the third and fourth portions such that a distance between an edge-end of the third edge portion and an edge-end of the fourth edge portion is a maximum distance between edges of the wound. The method includes: a first step of connecting the first edge portion and the second edge portion with the suture thread, including passing the suture thread through a first position on a mucosal surface of at least one of the first edge portion and the second edge portion; and a second step of connecting the third edge portion and the fourth edge portion with the suture thread, including passing the suture thread through a third position on the mucosal surface of at least one of the third edge portion and the fourth edge portion. A shortest distance between the wound and the third position is larger than a shortest distance between the wound and the first position.

In a second aspect, a method for closing the wound includes: a first step of connecting the first edge portion and the second edge portion with the suture thread, including passing the suture thread through a first position on a mucosal surface of at least one of the first edge portion and the second edge portion and a second position on the mucosal surface away from the first position; and a second step of connecting the third edge portion and the fourth edge portion with the suture thread, including passing the suture thread through a third position on the mucosal surface of at least one of the third edge portion and the fourth edge portion and a fourth position on the mucosal surface away from the third position. In this method, a second distance between the third position and the fourth position is smaller than a first distance between the first position and the second position.

DETAILED DESCRIPTION OF THE PREFERRED EMBODIMENTS

Figure 1:
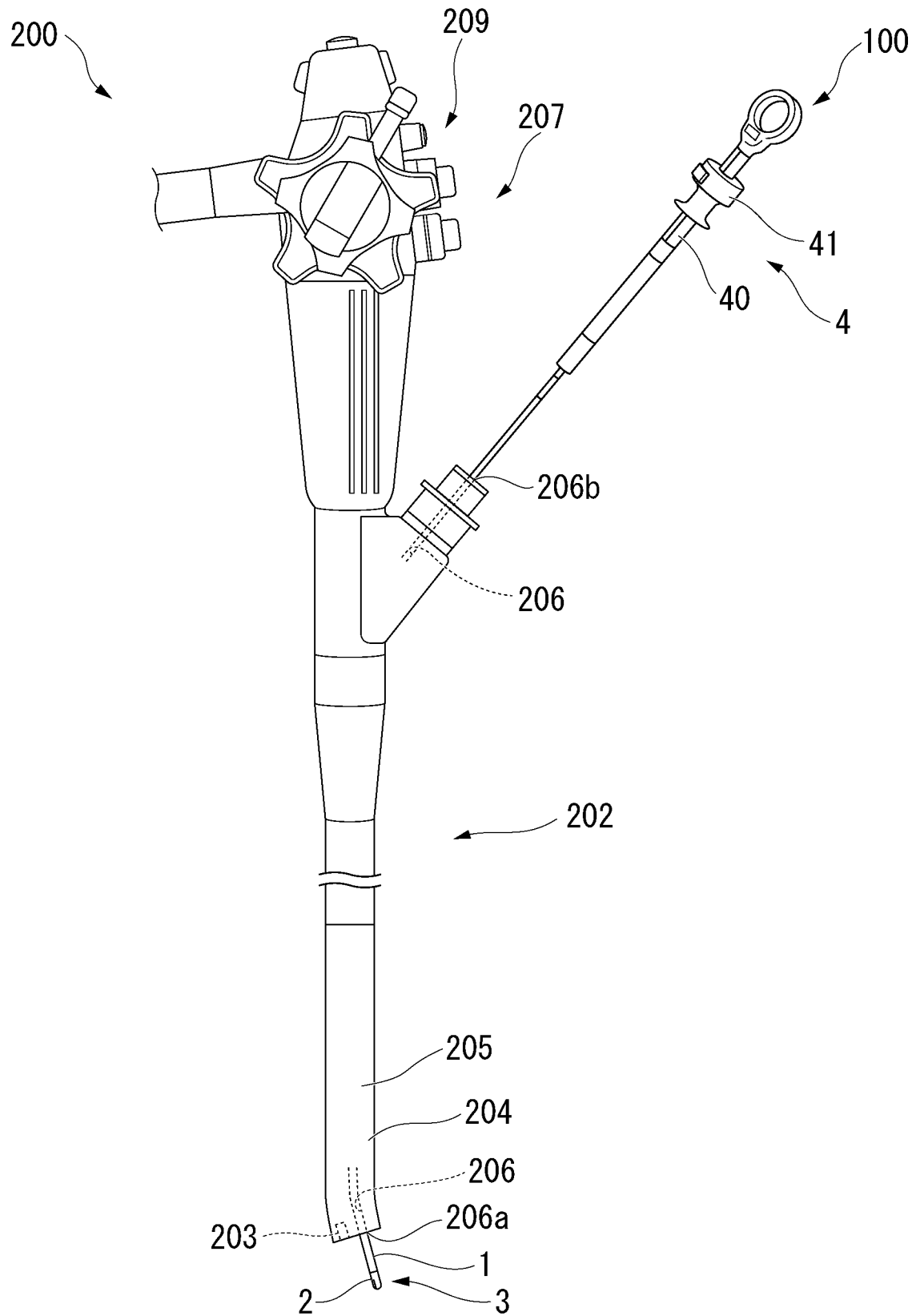
FIG. 1 is a diagram showing an endoscope and a needle holder used in a wound closing method according to an exemplary embodiment.

A wound closing method according to an exemplary embodiment of the present disclosure will be described with reference to FIGS. 1 to 24. FIG. 1 is a diagram showing an endoscope 200 and a needle holder 100 used in the wound closing method according to the present embodiment.

[Endoscope 200]

The surgeon can use a known endoscope that is orally inserted into a tubular organ such as a gastrointestinal tract. As shown in FIG. 1, the endoscope 200 used in the present embodiment includes an insertion portion 202 inserted into a body from a distal end and an operation portion 207 attached to a proximal end of the insertion portion 202.

The insertion portion 202 has an imaging portion 203, a curved portion 204, and a flexible portion 205. The imaging portion 203, the curved portion 204, and the flexible portion 205 are connected in order from the distal end of the insertion portion 202. A channel 206 for inserting the needle holder 100 is provided inside the insertion portion 202. A distal end opening 206a of the channel 206 is provided at the distal end of the insertion portion 202.

The imaging portion 203 includes, for example, a CCD or CMOS, and can image a portion to be treated. The imaging portion 203 can image a grip portion 3 of the needle holder 100 in a state where the needle holder 100 protrudes from the distal end opening 206a of the channel 206. The curved portion 204 can be bent according to the operation of the operating portion 207 by the surgeon. The flexible portion 205 is a flexible tubular portion.

The operation portion 207 is connected to the flexible portion 205. The operation portion 207 has an input portion 209 and a proximal end opening 206b of the channel 206. The input portion 209 receives an operation input for bending the curved portion 204.

[Needle holder 100]

Figure 2:
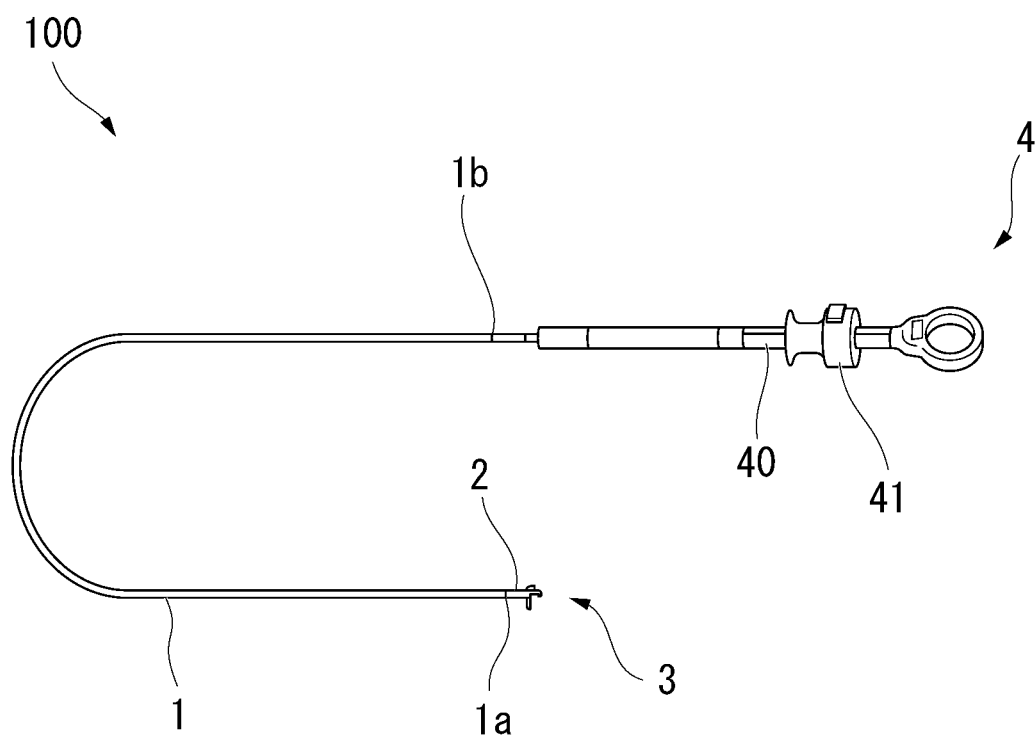
FIG. 2 is an overall view showing the needle holder.

FIG. 2 is an overall view showing the needle holder 100.

The needle holder 100 includes a sheath 1, a hard portion 2, a grip portion 3, an operation portion 4, and an operation wire 5 (see FIG. 3) inserted through the sheath 1. The needle holder 100 is used by inserting it into the channel 206 of the endoscope 200.

The sheath 1 is a flexible member that extends from a distal end 1a to a proximal end 1b. As shown in FIG. 1, in a state where the sheath 1 is inserted into the channel 206, the distal end 1a of the sheath 1 can be recessed from the distal end opening 206a of the channel 206. As shown in FIG. 2, the distal end 1a of the sheath 1 is provided with the hard portion 2. The operation portion 4 is provided at the proximal end 1b of the sheath 1.

Figure 3:
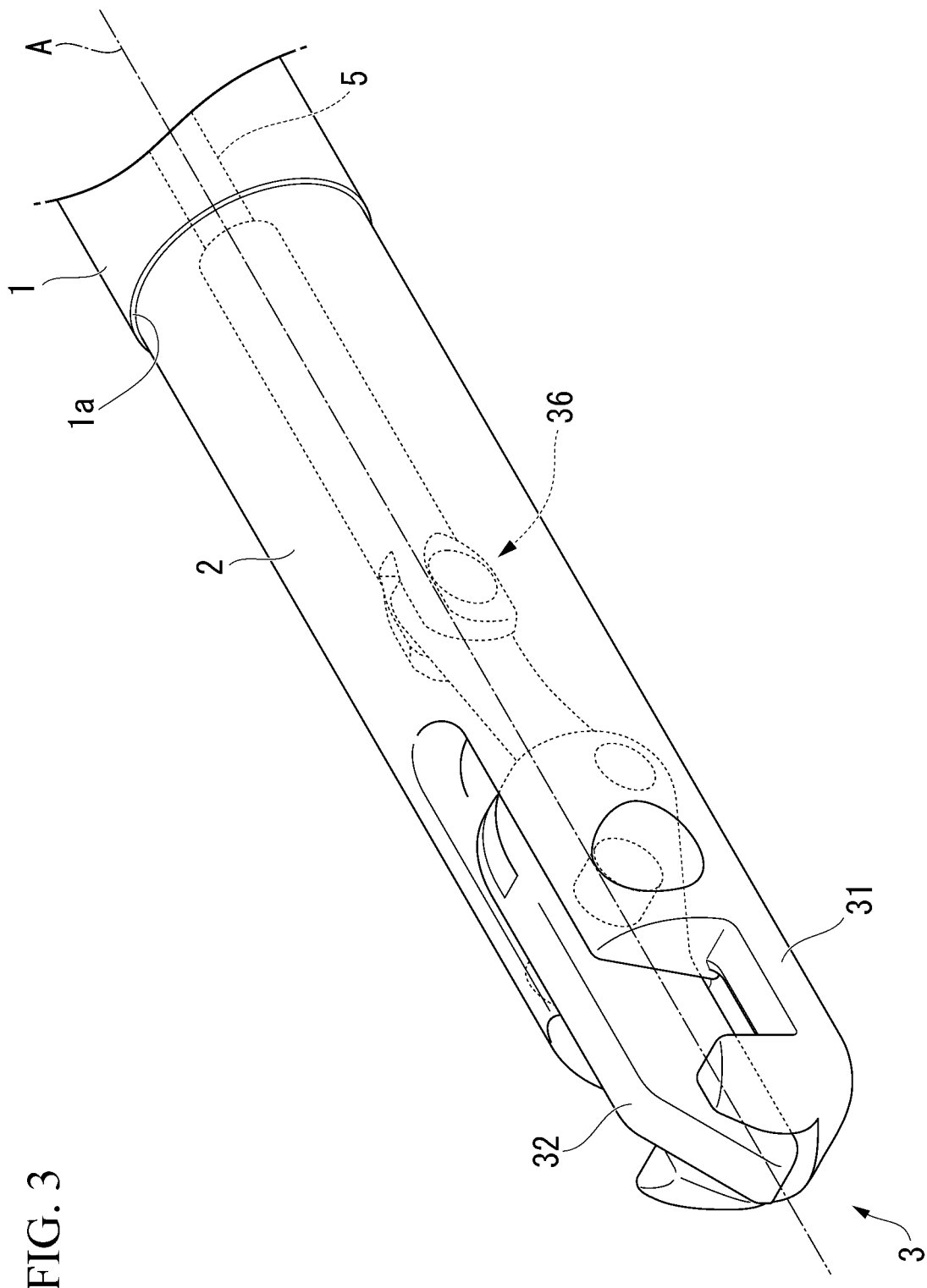
FIG. 3 is a perspective view showing a grip portion of the needle holder.

FIG. 3 is a perspective view showing the grip portion 3 of the needle holder 100.

The grip portion 3 has a first grip member 31, a second grip member 32, and a link mechanism 36. The first grip member 31 and the second grip member 32 are configured to be openable and closable.

The first grip member 31 is a part of the distal end portion of the hard portion 2. The first grip member 31 extends along the longitudinal axis A of the sheath 1. The second grip member 32 is connected to the hard portion 2 so as to be openable and closable with respect to the first grip member 31.

As shown in FIG. 2, the operation portion 4 has a main body 40 and a slider 41. The slider 41 is connected to the main body 40 so as to be able to move forward and backward, and can move forward and backward along the axial direction of the main body 40. The operation wire 5 extending from the sheath 1 passes through the inside of the main body 40 and is connected to the slider 41.

As shown in FIG. 3, the operation wire 5 is arranged inside the sheath 1 along the longitudinal axis A of the sheath 1. The surgeon can move the operating wire 5 forward and backward along the longitudinal axis A of the sheath 1 by moving the slider 41 forward and backward along the main body 40. The surgeon can pull the operation wire 5 toward the operation portion 4 by moving the slider 41 toward the proximal end side along the main body 40.

When the operation wire 5 is pulled toward the operation portion 4, the second grip member 32 moves in the closing direction with respect to the first grip member 31. On the other hand, when the operation wire 5 is pushed toward the grip portion 3, the second grip member 32 moves in the opening direction with respect to the first grip member 31.

[Closing the Wound]

Next, the wound closing method (method of using the needle holder 100) according to the present embodiment will be described with reference to FIGS. 4A to 24. Specifically, a procedure for closing a portion (wound W) in which the mucosa of the digestive tract is defective by ESD (endoscopic submucosal dissection) treatment will be described. The wound closing method according to the present embodiment is not limited to a wound in the digestive tract, and can be applied to a wound in a tubular organ.

Before inserting the endoscope 200 into the gastrointestinal tract, the surgeon protrudes the grip portion 3 of the needle holder 100 from the distal end opening 206a of the channel 206 of the endoscope 200. The surgeon grips the suture needle N with the grip portion 3. The suture needle N used in this embodiment is a curved needle. The treatment tool used in the wound closing method according to the present embodiment is not limited to the needle holder 100, and may be a treatment tool capable of gripping the suture needle N.

[Insert step]

Figure 4A:
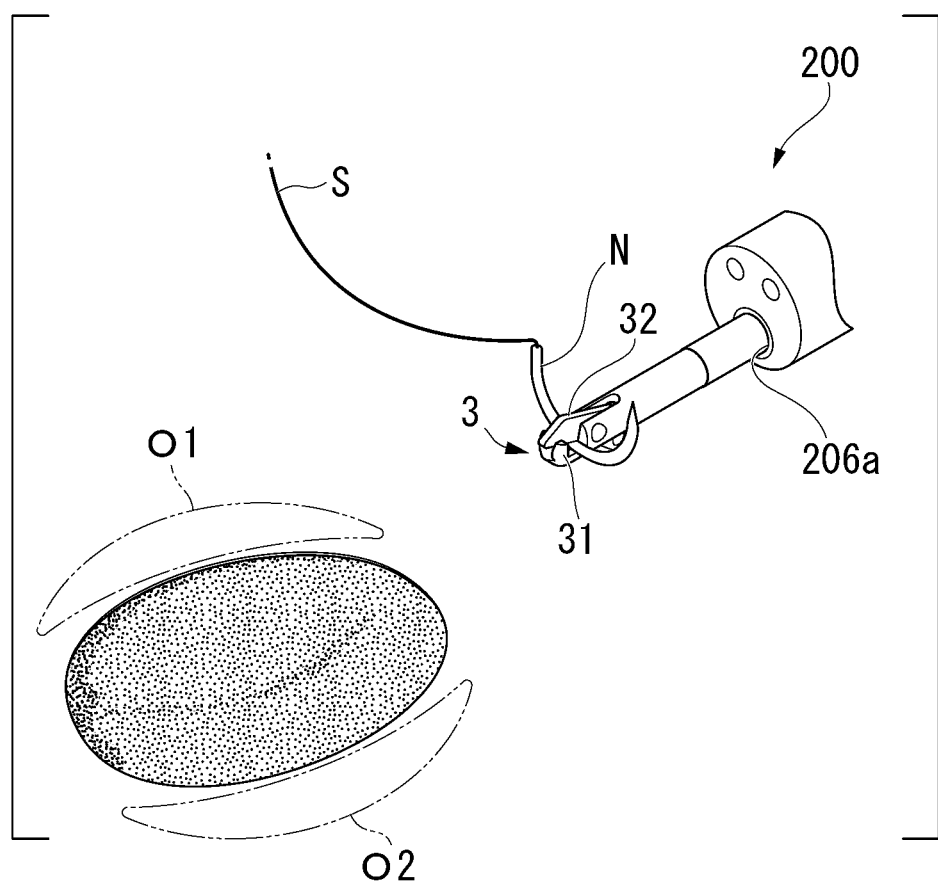
FIG. 4A is a diagram showing an insertion portion of the endoscope introduced into a gastrointestinal tract.

FIG. 4A is a diagram showing an insertion portion 202 of the endoscope 200 introduced into the gastrointestinal tract.

Figure 4B:
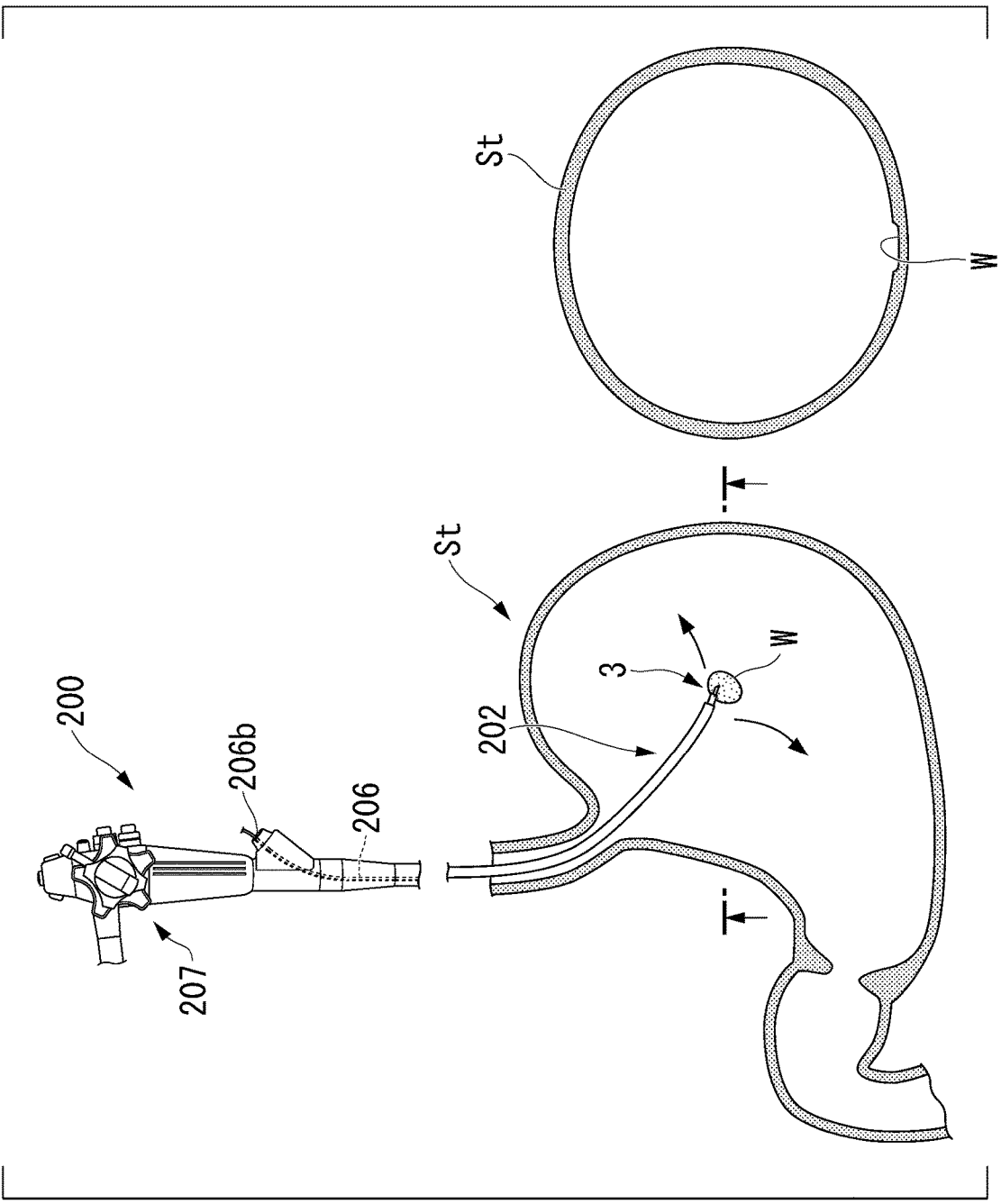
FIG. 4B is a diagram showing an insertion step when a tubular organ is a stomach.
Figure 4C:
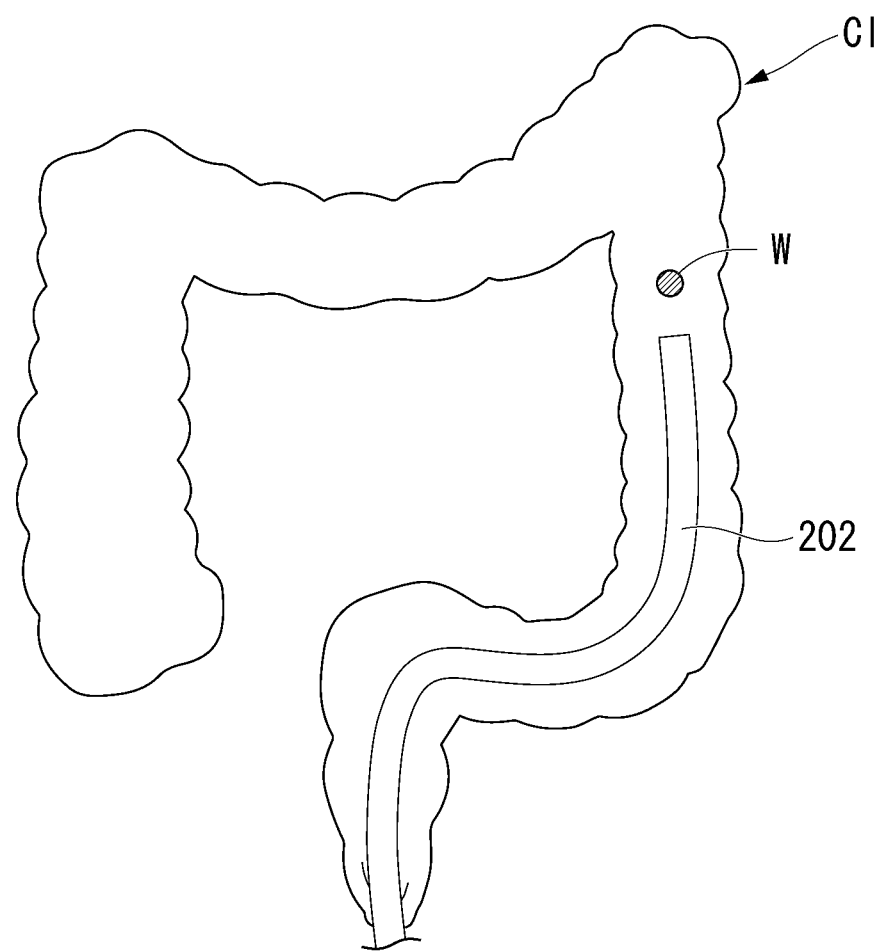
FIG. 4C is a diagram showing an insertion step when the tubular organ is a large intestine.

In the insertion step, the surgeon inserts the endoscope 200 into the gastrointestinal tract through the patient's natural opening. The insertion portion 202 is introduced into the digestive tract with the suture needle N gripped by the grip portion 3 protruding from the distal end opening 206a. FIG. 4B is a diagram showing the insertion step when the tubular organ is the stomach St. The right side of FIG. 4B is a cross-sectional view of the stomach St. Further, FIG. 4C is a diagram showing the insertion step when the tubular organ is the large intestine Cl.

[Placement Step]

Figure 5:
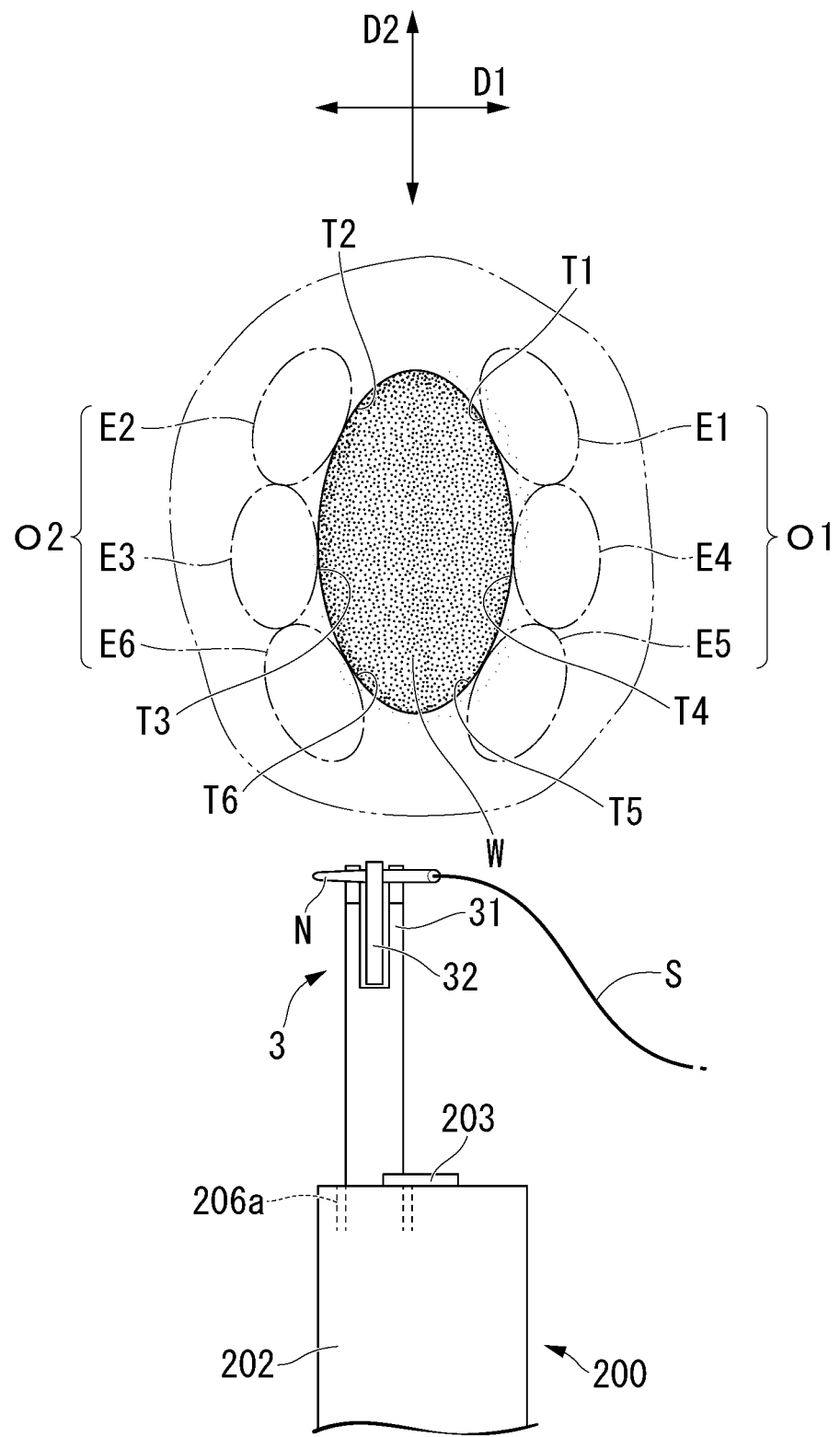
FIG. 5 is a top view of the insertion portion arranged to close the wound.

FIG. 5 is a top view of the insertion portion 202 arranged for closing the wound W.

In the placement step, the surgeon determines a first facing edge portion O1 and a second facing edge portion O2 to be brought close through the suture thread S to close the wound W. The first facing edge portion O1 and the second facing edge portion O2 are edge portions forming the peripheral edge of the wound W. The first facing edge portion O1 and the second facing edge portion O2 are at positions facing each other with the wound W sandwiched between them.

In the following description, the direction in which the first facing edge portion O1 and the second facing edge portion O2 face each other is also referred to as "width direction D1 of the wound W". Further, the direction along the wound W and perpendicular to the width direction D1 is also referred to as "depth direction D2 of the wound W".

The surgeon arranges the distal end of the insertion portion 202 of the endoscope 200 so that the grip portion 3 protruding from the insertion portion 202 of the endoscope 200 passes between the first facing edge portion O1 and the second facing edge portion O2. As a result, the suture needle N gripped by the grip portion 3 of the needle holder 100 is arranged at a position where it can easily be inserted into the first facing edge portion O1 and the second facing edge portion O2.

The first facing edge portion O1 has a first edge portion E1, a fourth edge portion E4, and a fifth edge portion E5. The first edge portion E1, the fourth edge portion E4, and the fifth edge portion E5 are regions extending along the depth direction D2. The first edge portion E1 and the fourth edge portion E4 are adjacent to each other, and the fourth edge portion E4 and the fifth edge portion E5 are adjacent to each other. The first edge portion E1 is located, for example, proximal to the endoscope 200 from the fourth edge portion E4. In that case, the fifth edge portion E5 is located distal to the endoscope 200 from the fourth edge portion E4.

On the wound W side of the first edge portion E1, an edge-end T1, which is a cut surface caused by a tissue defect, is formed. Further, an edge-end T4, which is a cut surface generated by a tissue defect, is formed on the wound W side of the fourth edge portion E4. Further, an edge-end T5, which is a cut surface generated by a tissue defect, is formed on the wound W side of the fifth edge portion E5.

The second facing edge portion O2 has a second edge portion E2, a third edge portion E3, and a sixth edge portion E6. The second edge portion E2, the third edge portion E3, and the sixth edge portion E6 are regions extending along the depth direction D2. The second edge portion E2 and the third edge portion E3 are adjacent to each other, and the third edge portion E3 and the sixth edge portion E6 are adjacent to each other. The second edge portion E2 is located, for example, proximal to the endoscope 200 from the third edge portion E3. In that case, the sixth edge portion E6 is located distal to the endoscope 200 from the third edge portion E3.

On the wound W side of the second edge portion E2, an edge-end T2, which is a cut surface caused by a tissue defect, is formed. Further, an edge-end T3, which is a cut surface generated by a tissue defect, is formed on the wound W side of the third edge portion E3. Further, an edge-end T6, which is a cut surface generated by a tissue defect, is formed on the wound W side of the sixth edge portion E6.

The first edge portion E1 and the second edge portion E2 are located so as to face each other with the wound W in between. Further, the third edge portion E3 and the fourth edge portion E4 are at positions facing each other with the wound W in between. Further, the fifth edge portion E5 and the sixth edge portion E6 are located at positions facing each other with the wound W in between.

At the peripheral edge of the wound W, the distance between the edge-ends of the facing edges is the largest between the edge-end T3 of the third edge portion E3 and the edge-end T4 of the fourth edge portion E4. The distance between the edge-end T1 of the first edge portion E1 and the edge-end T2 of the second edge portion E2 is narrower than the distance between the edge-end T3 of the third edge portion E3 and the edge-end T4 of the fourth edge portion E4. The distance between the edge-end T5 of the fifth edge portion E5 and the edge-end T6 of the sixth edge portion E6 is narrower than the distance between the edge-end T3 of the third edge portion E3 and the edge-end T4 of the fourth edge portion E4.

The wound closing method according to the present embodiment includes: a first step of connecting the first edge portion E1 and the second edge portion E2 with the suture thread S; a second step of connecting the third edge portion E3 and the fourth edge portion E4 with the suture thread S; and a third step of connecting the fifth edge portion E5 and the sixth edge portion E6 with the suture thread S.

Before the first step after placing the endoscope 200, the surgeon observes the first edge portion E1, the second edge portion E2, the third edge portion E3, the fourth edge portion E4, the fifth edge portion E5, and the sixth edge portion E6 of the wound W with the endoscope 200. If the surgeon determines that it is difficult to perform the first step, the surgeon performs the placement step again.

[First Step]

The first step includes: step A of passing the suture thread S through a first position P1 on the mucosal surface of the first edge portion E1; step B of passing the suture thread S through the second edge portion E2; a first suturing step of pulling the suture thread S; and step C of passing the suture thread S through a second position P2 away from the first position P1 on the mucosal surface of the first edge portion E1.

[Step A]

In step A, the surgeon passes the suture thread S through the first position P1 on the mucosal surface of the first edge portion E1. Step A includes: step A-1 of inserting the suture needle N into the first position P1 on the mucosal surface of the first edge portion E1; and step A-2 of piercing through the edge-end T1 of the first edge portion E1 with the suture needle N.

[Step A-1]

Figure 6:
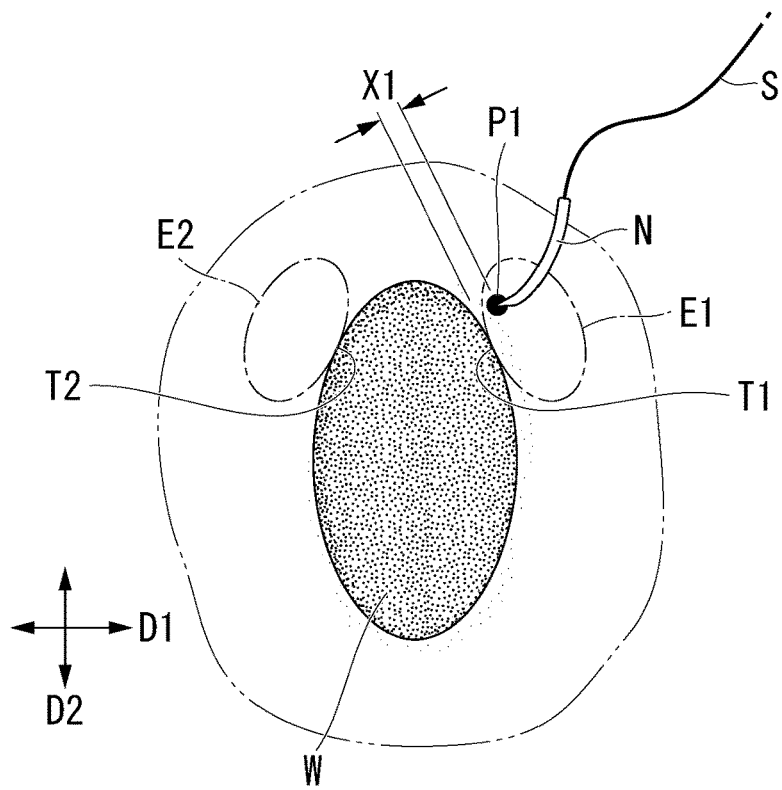
FIG. 6 is a diagram showing step A-1 in the wound closing method.
Figure 7:
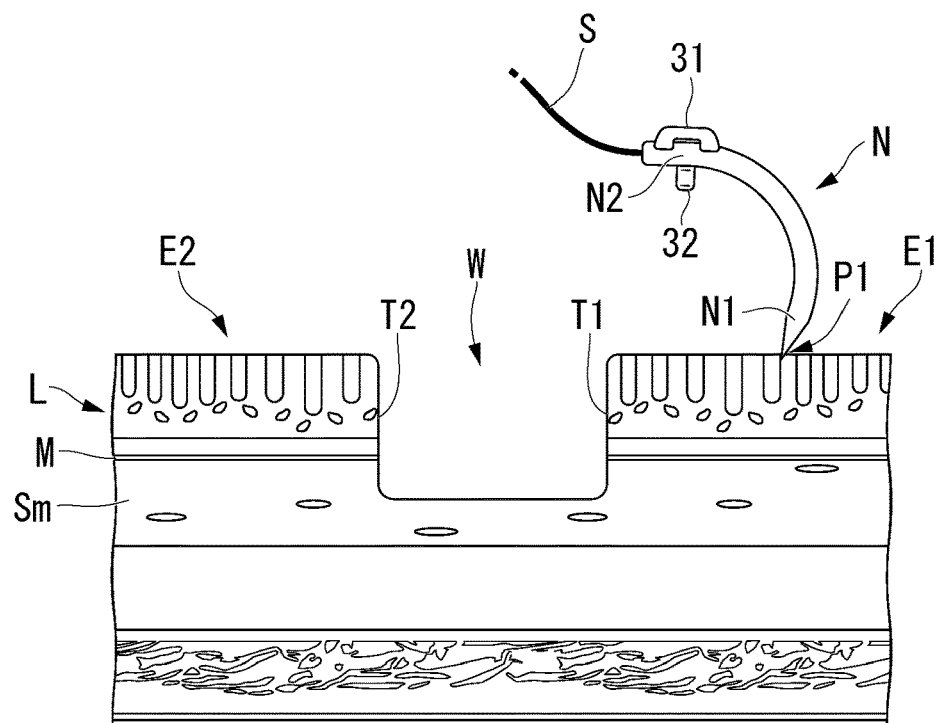
FIG. 7 is a cross-sectional view of the wound orthogonal to a depth direction in step A-1.

FIG. 6 is a diagram showing step A-1 in the wound closing method. FIG. 7 is a cross-sectional view of the wound W orthogonal to the depth direction D2 in step A-1. In the wound W, a mucosal layer L is removed and a submucosal layer Sm is exposed. A part of the submucosal layer Sm may be removed at the wound W. In step A-1, the surgeon rotates the grip portion 3 while gripping a rear end portion N2 of the suture needle N by the grip portion 3, and inserts a distal end portion N1 of the suture needle N into the first position P1 on the mucosal surface in the mucosal layer L of the first edge portion E1. In the following description, the shortest distance from the first position P1 to the wound W is referred to as "shortest distance X1".

[Step A-2]

Figure 8:
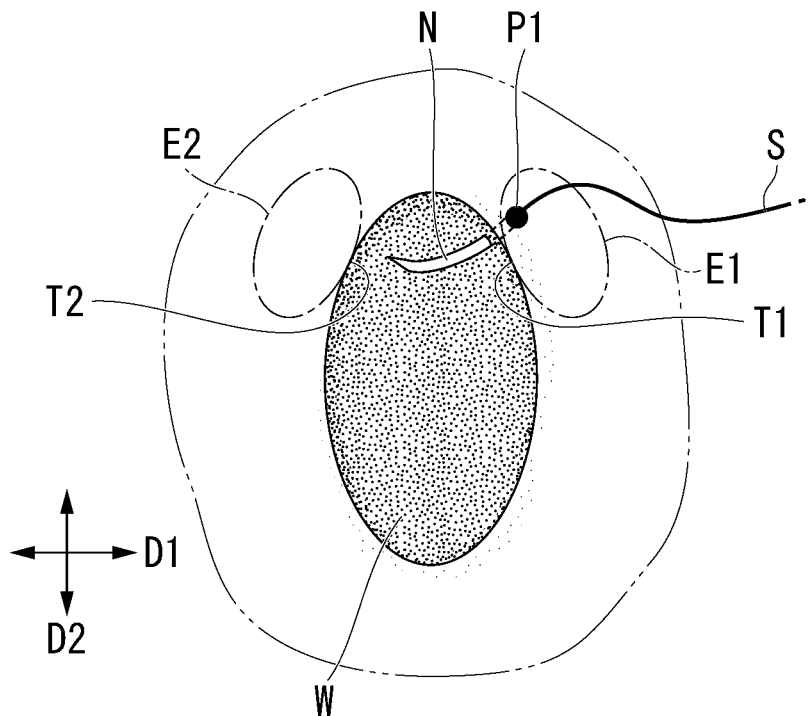
FIG. 8 is a diagram showing step A-2 in the wound closing method.
Figure 9:
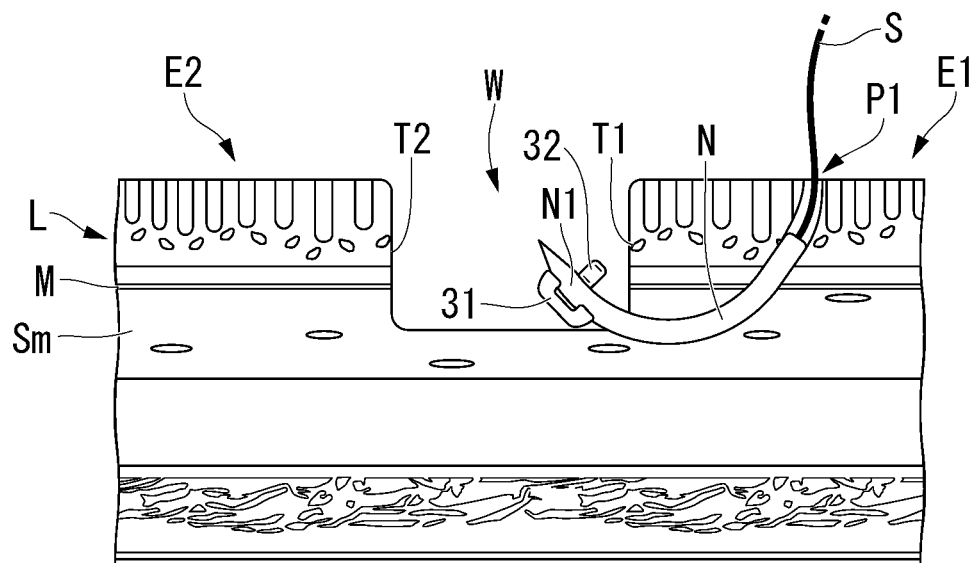
FIG. 9 is a cross-sectional view of the wound orthogonal to the depth direction in step A-2.

FIG. 8 is a diagram showing step A-2 in the wound closing method. FIG. 9 is a cross-sectional view of the wound W orthogonal to the depth direction D2 in step A-2. In step A-2, the surgeon pierces through the edge-end T1 of the first edge portion E1 with the suture needle N, which has been inserted into the first position P1 on the mucosal surface of the first edge portion E1. As shown in FIG. 9, the surgeon inserts the suture needle N from the submucosal layer Sm at the edge-end T1. The mucosal basal layer M shown in FIG. 9 is a part of the mucosal layer L and is a layer including a boundary surface in contact with the submucosal layer Sm. The mucosal basal layer M may also be referred to as a basement membrane.

Specifically, in step A-2, the surgeon further rotates the grip portion 3 while gripping the rear end portion N2 of the suture needle N by the grip portion 3, and protrudes the distal end portion N1 of the suture needle N from the edge-end T1 of the first edge portion E1. The surgeon may protrude the distal end portion N1 of the suture needle N from a wound surface of the wound W. Next, as shown in FIG. 9, the surgeon rotates the grip portion 3 while gripping the distal end portion N1 of the suture needle N protruding from the edge-end T1 with the grip portion 3, and removes the suture needle N from the edge-end T1.

[Step B]

In step B after step A, the surgeon passes the suture thread S through the second edge portion E2. Step B includes: step B-1 of inserting the suture needle N into the edge-end T2 of the second edge portion E2; and step B-2 of inserting the suture needle N from the mucosal surface of the second edge portion E2.

[Step B-1]

Figure 10:
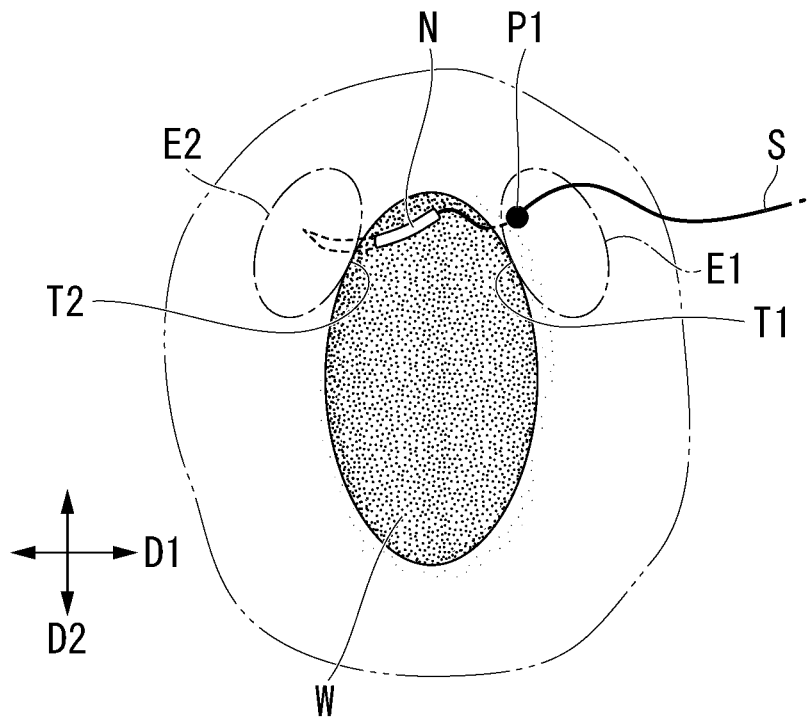
FIG. 10 is a diagram showing step B-1 in the wound closing method.
Figure 11:
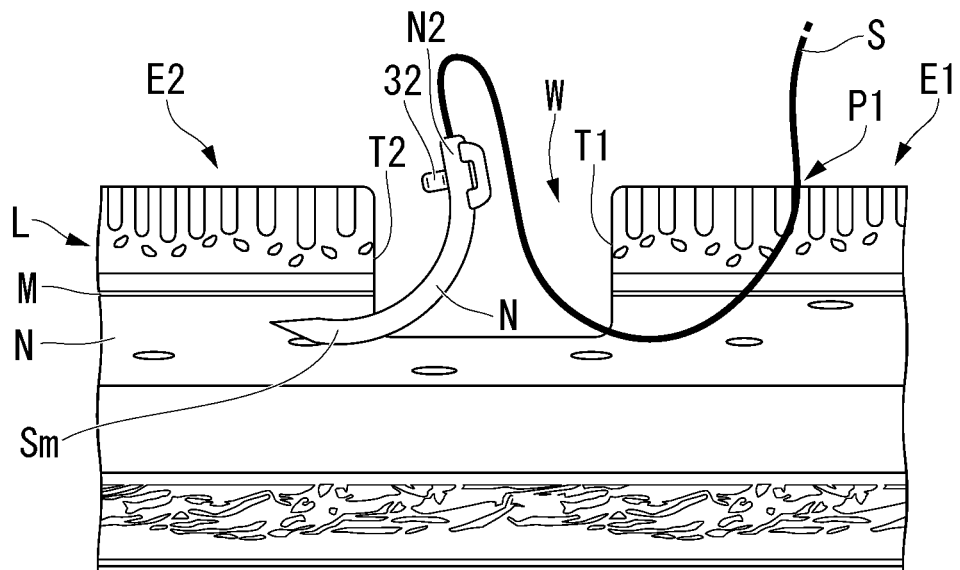
FIG. 11 is a cross-sectional view of the wound orthogonal to the depth direction in step B-1.

FIG. 10 is a diagram showing step B-1 in the wound closing method. FIG. 11 is a cross-sectional view of the wound W orthogonal to the depth direction D2 in step B-1. In step B-1, the surgeon rotates the grip portion 3 while gripping the rear end portion N2 of the suture needle N by the grip portion 3, and inserts the suture needle N, which has pierced through the edge-end T1 of the first edge portion E1, into the edge-end T2 of the second edge portion E2. As shown in FIG. 11, in step B-1, the surgeon inserts the suture needle N into the submucosal layer Sm at the edge-end T2. The surgeon may insert the suture needle N from the wound surface of the wound W.

[Step B-2]

Figure 12:
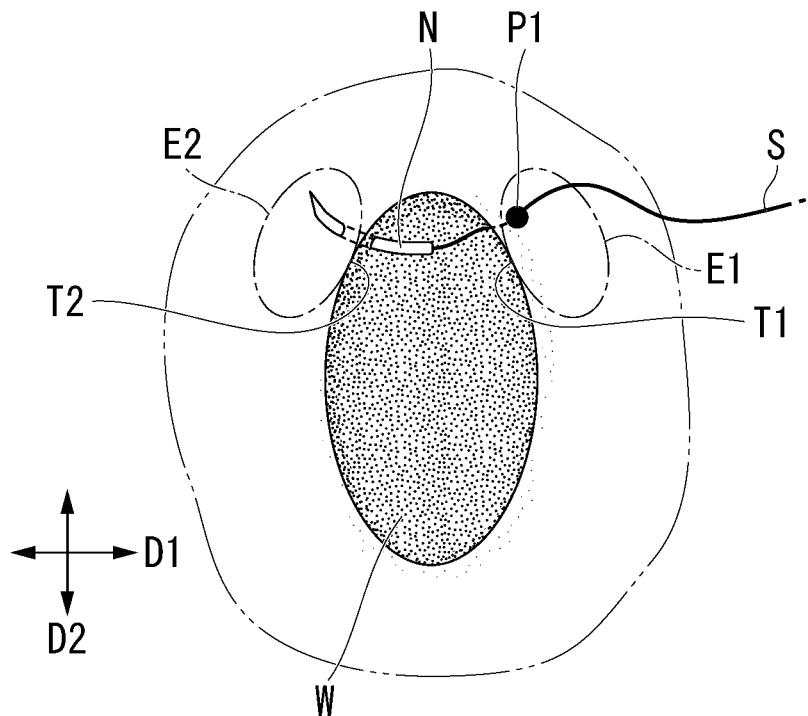
FIG. 12 is a diagram showing step B-2 in the wound closing method.
Figure 13:
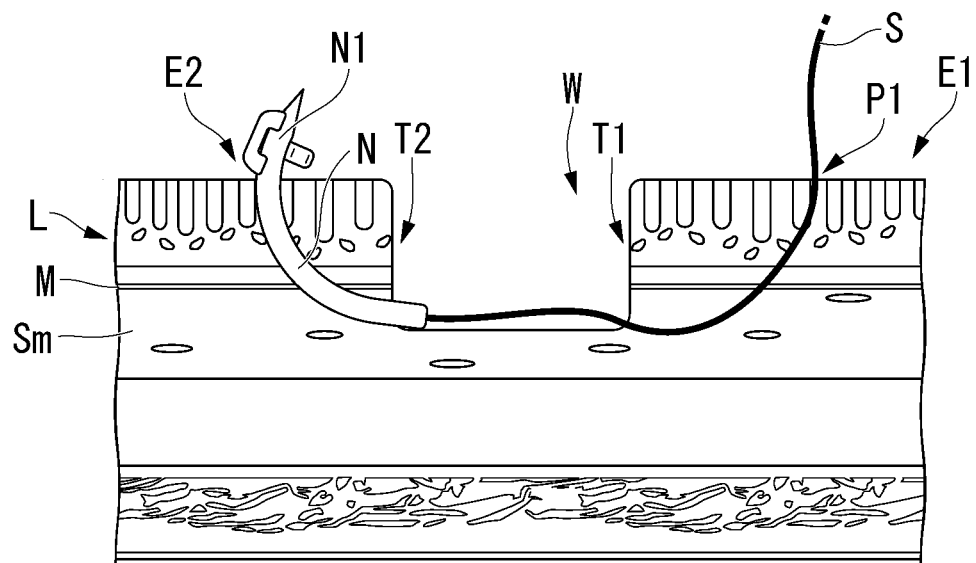
FIG. 13 is a cross-sectional view of the wound orthogonal to the depth direction in step B-2.

FIG. 12 is a diagram showing step B-2 in the wound closing method. FIG. 13 is a cross-sectional view of the wound W orthogonal to the depth direction D2 in step B-2. In step B-2, the surgeon pierces through the mucosal surface in the mucosal layer L of the second edge portion E2 with the suture needle N, which has been inserted into the edge-end T2 of the second edge portion E2.

Specifically, the surgeon further rotates the grip portion 3 while gripping the rear end portion N2 of the suture needle N by the grip portion 3, and protrudes the distal end portion N1 of the suture needle N from the mucosal surface of the second edge portion E2. Next, as shown in FIG. 13, the surgeon rotates the grip portion 3 while gripping the distal end portion N1 of the suture needle N protruding from the second edge portion E2 with the grip portion 3, and removes the suture needle N from the second edge portion E2.

[First Suturing Step]

Figure 14:
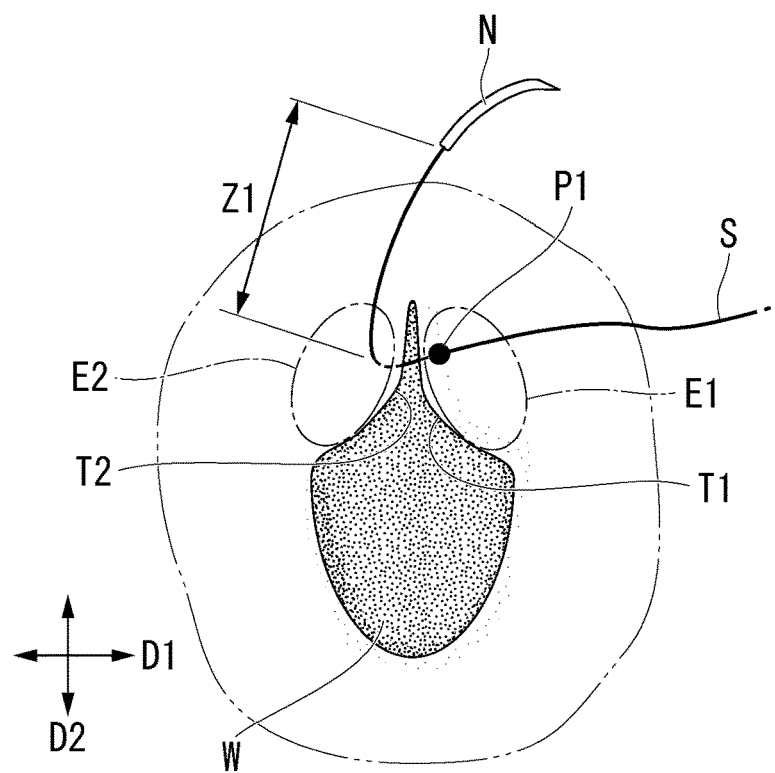
FIG. 14 is a diagram showing a first suturing step in the wound closing method.

FIG. 14 is a diagram showing a first suturing step in the wound closing method.

The surgeon pulls the suture thread S in the first suturing step after step B. The surgeon pulls the suture thread S by the first length Z1 by retracting the grip portion 3 that grips the suture needle N, for example. As a result, as shown in FIG. 14, the first edge portion E1 and the second edge portion E2 are close to each other.

After the first suturing step, the surgeon observes the proximity state of the first edge portion E1 and the second edge portion E2 with the endoscope 200. If the proximity is inadequate, the surgeon performs the first suturing step again.

After step B, if the first edge portion E1 and the second edge portion E2 are already sufficiently close to each other, or if there is not enough space for pulling the suture thread S, the surgeon May omit the first suturing step.

[Step C]

In step C after the first suturing step (after step B if the first suturing step has not been performed), the surgeon passes the suture thread S through the second position P2 away from the first position P1 on the mucosal surface of the first edge position E1. Step C includes: step C-1 of inserting the suture needle N into the second position P2 on the mucosal surface of the first edge portion E1; and step C-2 of piercing through the edge-end T1 of the first edge portion E1 with the suture needle N.

[Step C-1]

Figure 15:
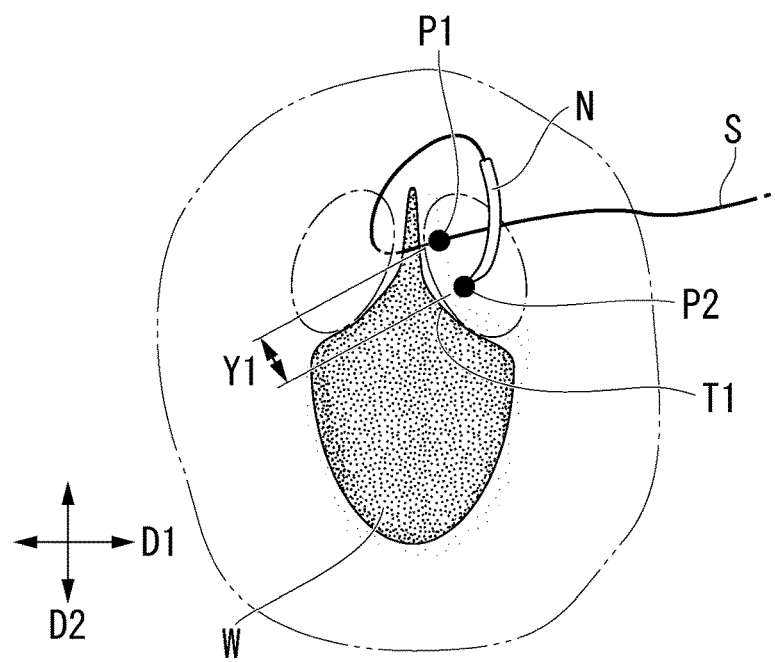
FIG. 15 is a diagram showing step C-1 in the wound closing method.

FIG. 15 is a diagram showing step C-1 in the wound closing method.

In step C-1, the surgeon inserts the suture needle N, which has pierced through the mucosal surface of the second edge portion E2, into the second position P2 on the mucosal surface in the mucosal layer L of the first edge portion E1 by the same method as in step A-1. In the following description, the distance between the first position P1 and the second position P2 is referred to as "first distance Y1".

[Step C-2]

Figure 16:
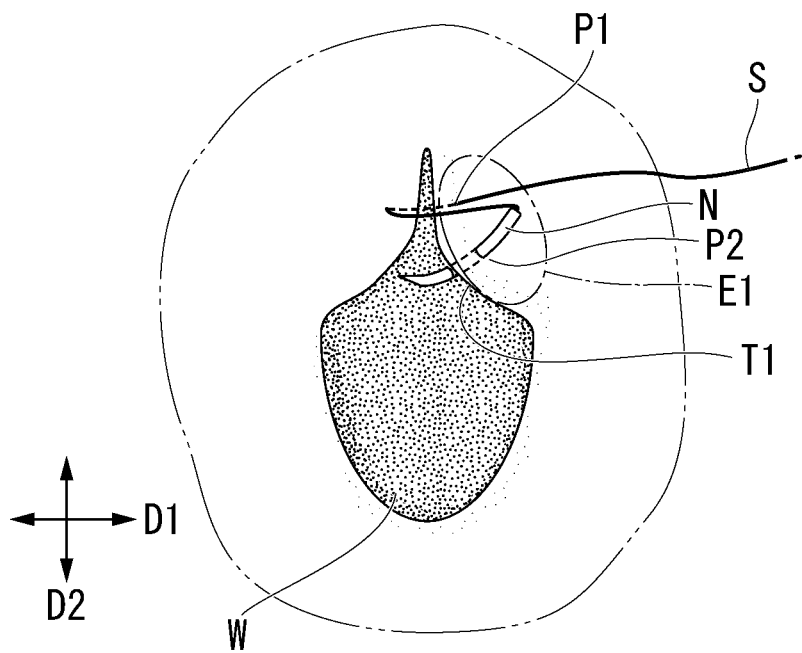
FIG. 16 is a diagram showing step C-2 in the wound closing method.

FIG. 16 is a diagram showing step C-2 in the wound closing method.

In step C-2, the surgeon inserts the suture needle N, which is inserted into the second position P2 on the mucosal surface of the first edge portion E1, from the edge-end T1 of the first edge portion E1 by the same method as in step A-2.

If the suture from step A to step C is not sufficiently performed over the depth direction D2 of the first edge portion E2 and the second edge portion E2, the surgeon repeats steps B and C.

[Second Step]

The second step includes: step D of passing the suture thread S through the third position P3 on the mucosal surface of the third edge portion E3; step E of passing the suture thread S through the fourth edge portion E4; step F of passing the suture thread S through the fourth position P4 away from the third position P3 on the mucosal surface of the third edge portion E3; and a second suturing step of pulling the suture thread S.

[Step D]

In step D after step C, the surgeon passes the suture thread S through the third position P3 on the mucosal surface of the third edge portion E3. Step D includes: step D-1 of inserting the suture needle N into the edge-end T3 of the third edge portion E3; and step D-2 of piercing through the third position P3 on the mucosal surface of the third edge portion E3 with the suture needle N.

[Step D-1]

Figure 17:
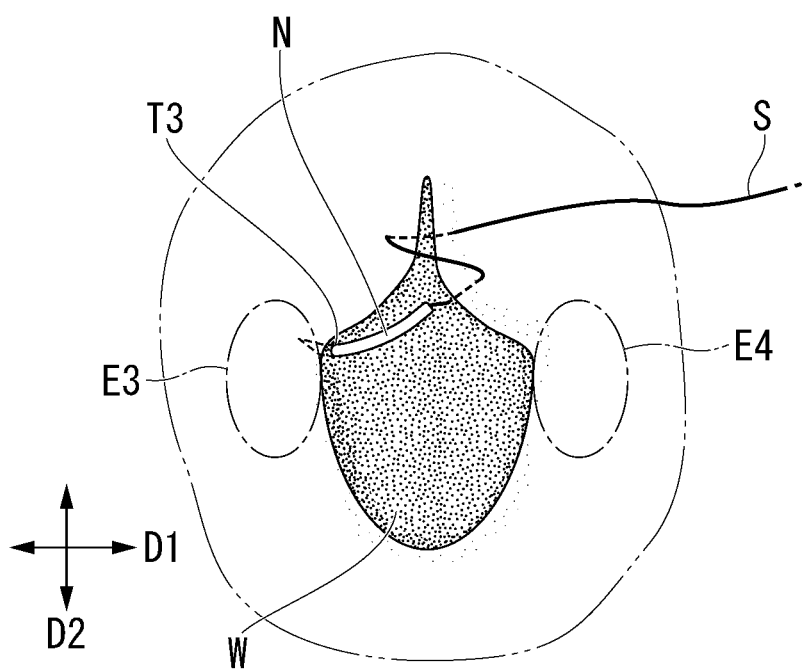
FIG. 17 is a diagram showing step D-1 in the wound closing method.

FIG. 17 is a diagram showing step D-1 in the wound closing method.

In step D-1, the surgeon inserts the suture needle N, which has pierced through the edge-end T1 of the first edge portion E1, into the edge-end T3 of the third edge portion E3 by the same method as in step B-1.

[Step D-2]

Figure 18:
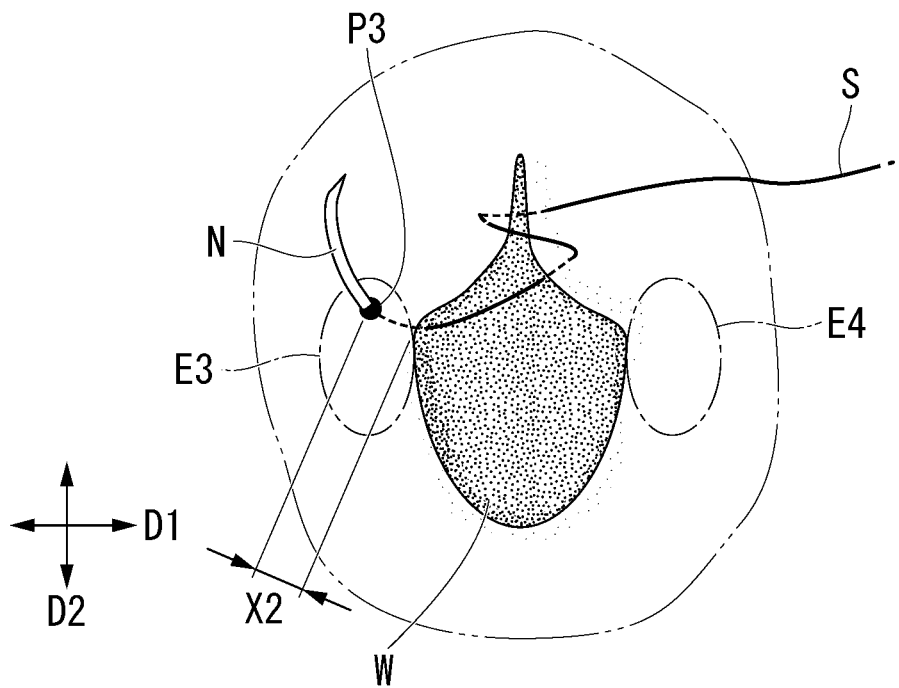
FIG. 18 is a diagram showing step D-2 in the wound closing method.

FIG. 18 is a diagram showing step D-2 in the wound closing method.

In step D-2, the surgeon pierces through the third position P3 on the mucosal surface in the mucosal layer L of the third edge portion E3 with the suture needle N, which has been inserted into the edge-end T3 of the third edge portion E3, by the same method as in step B-2. In the following description, the shortest distance from the third position P3 to the wound W is referred to as "shortest distance X2". The shortest distance X2 is larger than the shortest distance X1 (see FIG. 6).

[Step E]

In step E after step D, the surgeon passes the suture thread S through the fourth edge portion E4. Step E includes: step E-1 of inserting the suture needle N into the mucosal surface in the mucosal layer L of the fourth edge portion E4, and step E-2 of piercing through the edge-end T4 of the fourth edge portion E4 with the suture needle N.

[Step E-1]

Figure 19:
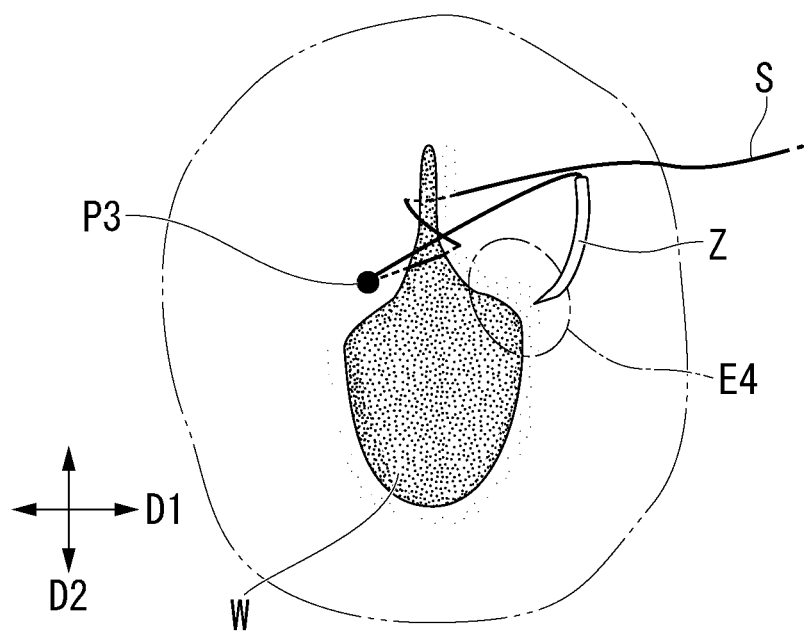
FIG. 19 is a diagram showing step E-1 in the wound closing method.

FIG. 19 is a diagram showing step E-1 in the wound closing method.

In step E-1, the surgeon inserts the suture needle N, which has pierced through the third position P3 on the mucosal surface of the third edge portion E3, into the mucosal surface in the mucosal layer L of the fourth edge portion E4 by the same method as in step A-1.

[Step E-2]

Figure 20:
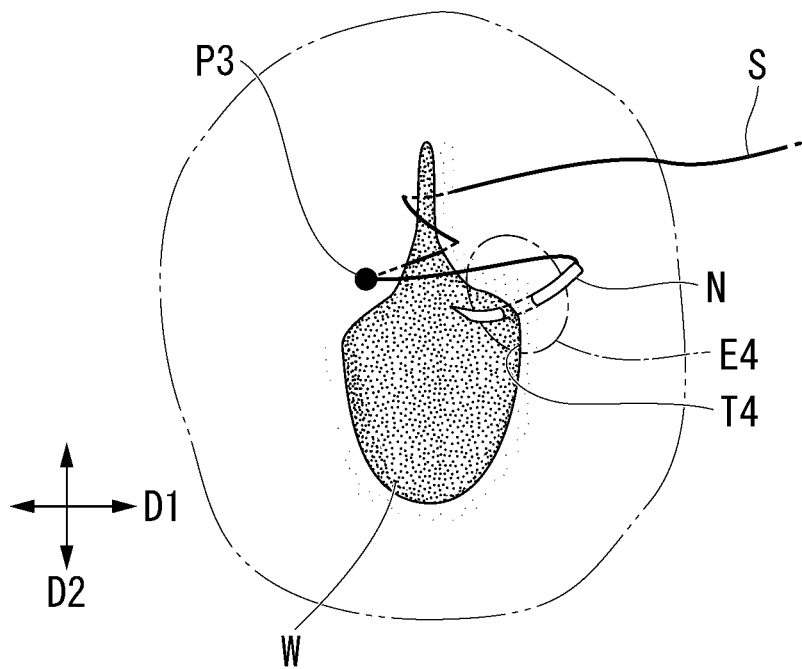
FIG. 20 is a diagram showing step E-2 in the wound closing method.

FIG. 20 is a diagram showing step E-2 in the wound closing method.

In step E-2, the surgeon pierces through the edge-end T4 of the fourth edge portion E4 by the same method as in step A-2 with the suture needle N, which has been inserted into the mucosal surface of the fourth edge portion E4.

[Step F]

In step F after step E, the surgeon passes the suture thread S through the fourth position P4 away from the third position P3 on the mucosal surface of the third edge portion E3. Step F includes step F-1 of inserting the suture needle N into the edge-end T3 of the third edge portion E3, and step F-2 of inserting the suture needle N from the fourth position P4 on the mucosal surface of the third edge portion E3.

[Step F-1]

Figure 21:
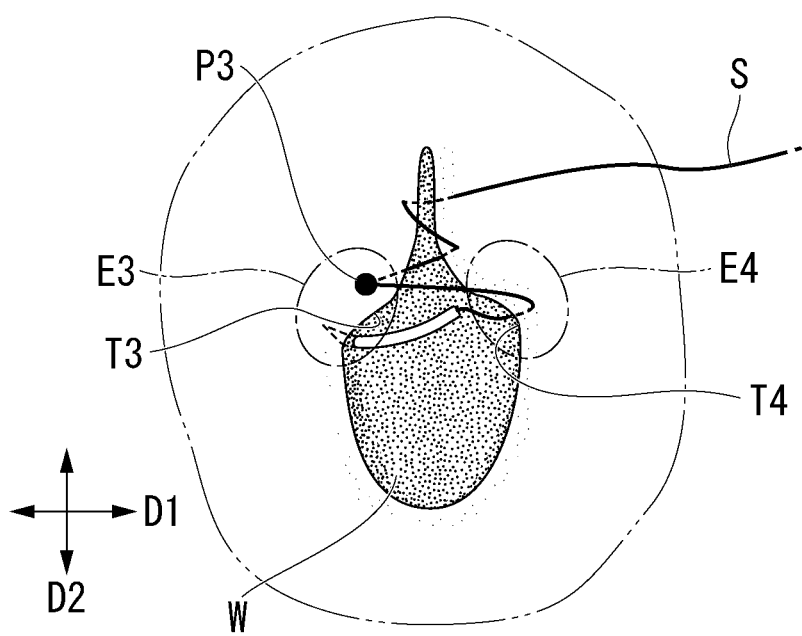
FIG. 21 is a diagram showing step F-1 in the wound closing method.

FIG. 21 is a diagram showing step F-1 in the wound closing method.

In step F-1, the surgeon inserts the suture needle N, which has pierced through the edge-end T4 of the fourth edge portion E4, into the edge-end T3 of the third edge portion E3 by the same method as in step B-1.

[Step F-2]

Figure 22:
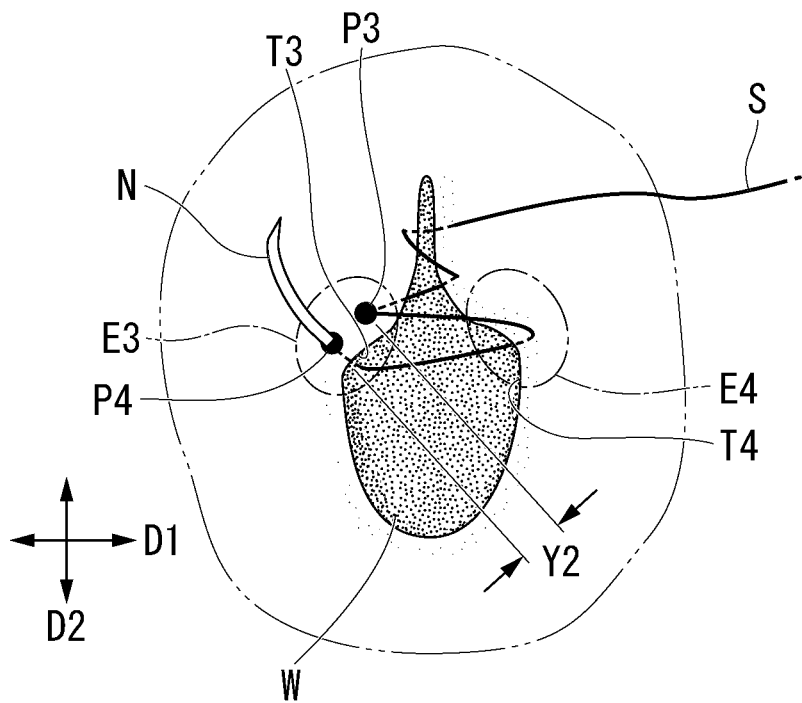
FIG. 22 is a diagram showing step F-2 in the wound closing method.

FIG. 22 is a diagram showing step F-2 in the wound closing method.

In step F-2, the surgeon pierces through the fourth position P4 on the mucosal surface in the mucosal layer L of the third edge portion E3 with the suture needle N, which has been inserted into the edge-end T3 of the third edge portion E3, by the same method as in step B-2. In the following description, the distance between the third position P3 and the fourth position P4 will be referred to as "second distance Y2".

[Second Suturing Step]

Figure 23:
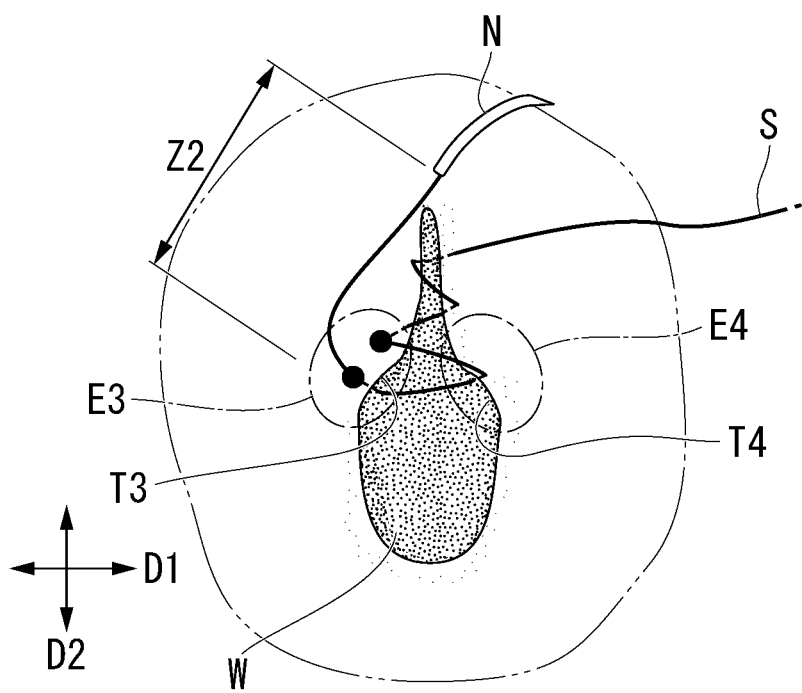
FIG. 23 is a diagram showing a second suturing step in the wound closing method.

FIG. 23 is a diagram showing a second suturing step in the wound closing method.

The surgeon pulls the suture thread S in the second suturing step after step F. The surgeon pulls the suture thread S by a second length Z2 by, for example, retracting the grip portion 3 that grips the suture needle N. As a result, as shown in FIG. 23, the third edge portion E3 and the fourth edge portion E4 are close to each other.

It is desirable that the second length Z2 be larger than the first length Z1. A portion of the wound W having a large distance in the width direction D1 can be sufficiently sutured by increasing the pulling amount of the suture thread S.

After the second suturing step, the surgeon observes the proximity state of the third edge portion E3 and the fourth edge portion E4 with the endoscope 200. If the proximity is inadequate, the surgeon performs the second suturing step again.

After step F, when the third edge portion E3 and the fourth edge portion E4 are already sufficiently close to each other, or when there is not enough space for pulling the suture thread S, the surgeon may omit the second suturing step.

If the suturing from step D to step F is not sufficiently performed over the depth direction D2 of the third edge portion E3 and the fourth edge portion E4, the surgeon repeats step D to step F.

[Third Step]

In the third step, the fifth edge portion E5 and the sixth edge portion E6 are connected by the suture thread S by the same method as in the first step. The third step includes: step G of passing the suture thread S through the mucosal surface of the fifth edge portion E5 by the same method as in step A; step H of passing the suture thread S through the sixth edge portion E6 by the same method as in step B; a third suturing step of pulling the suture thread S by the same method as the first suturing step; and step I of passing the suture thread S through the mucosal surface of the fifth edge portion E5 by the same method as step C.

Finally, the surgeon ends the procedure by tying a knot on the suture thread S. If the suture thread S has a plurality of barbs and is a suture thread S that allows movement only in the direction in which the suture needle N is attached, a knot is not always necessary.

Figure 24:
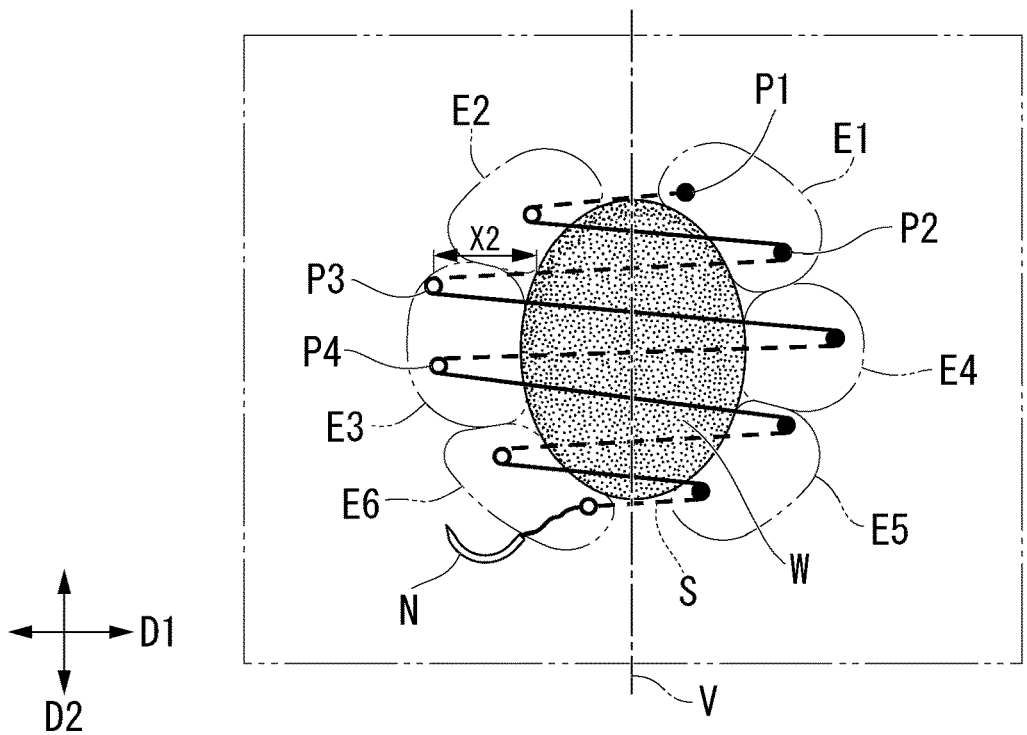
FIG. 24 is a diagram showing a suture thread passed through the wound.

FIG. 24 is a diagram showing a suture thread S passed through the wound W. The suture thread S shown in FIG. 24 is not sutured. The shortest distance X2 from the third position P3 to the wound W is larger than the shortest distance X1 from the first position P1 to the wound W. The distance between the edge-end T3 of the third edge portion E3 and the edge-end T4 of the fourth edge portion E4 is maximum among the distances between the edge-ends of the edges facing each other on the peripheral edge of the wound W. Therefore, after closing, the force that causes the third edge portion E3 and the fourth edge portion E4 to be separated from each other becomes the largest at the peripheral edge of the wound W. However, since the shortest distance X2 is larger than the shortest distance X1, even when the force for separating the third edge portion E3 is large, the suture thread S does not easily come off from the third edge portion E3.

The shortest distance X1 can also be defined as the distance in the direction in which the suture thread S is sewn and intersects the virtual surface V from the virtual surface V where the first facing edge portion O1 (first edge portion E1, fourth edge portion E4, fifth edge portion E5) and the second facing edge portion O2 (second edge portion E2, third edge portion E3, sixth edge portion E6) meet the first position P1. Further, the shortest distance X2 can also be defined as the distance from the virtual surface V to the third position P3. The greater the distance from the virtual surface V to the position where the suture thread S is passed, the more difficult it is for the suture thread S to come off from the edge.

According to the wound closing method according to the present embodiment, even a large wound W that cannot be closed by a clip can be suitably closed. The larger the defect of the wound W, the stronger the force to separate the first facing edge portion O1 and the second facing edge portion O2 after closing. According to the wound closing method according to the present embodiment, by increasing the shortest distance X2 from the third position P3 through which the suture thread S is passed through the third edge portion E3 where the force to be separated is maximum to the wound W (virtual surface V), the suture thread S does not easily come off from the third edge portion E3. As a result, the wound closing method according to the present embodiment can suitably close even a large wound W.

Although the above embodiment of the present disclosure has been described in detail with reference to the drawings, the specific configuration is not limited to this embodiment, and includes design changes and the like within a range that does not deviate from the gist of the present disclosure. In addition, the components shown in the above-described embodiments and modifications can be appropriately combined and configured.

Figure 25:
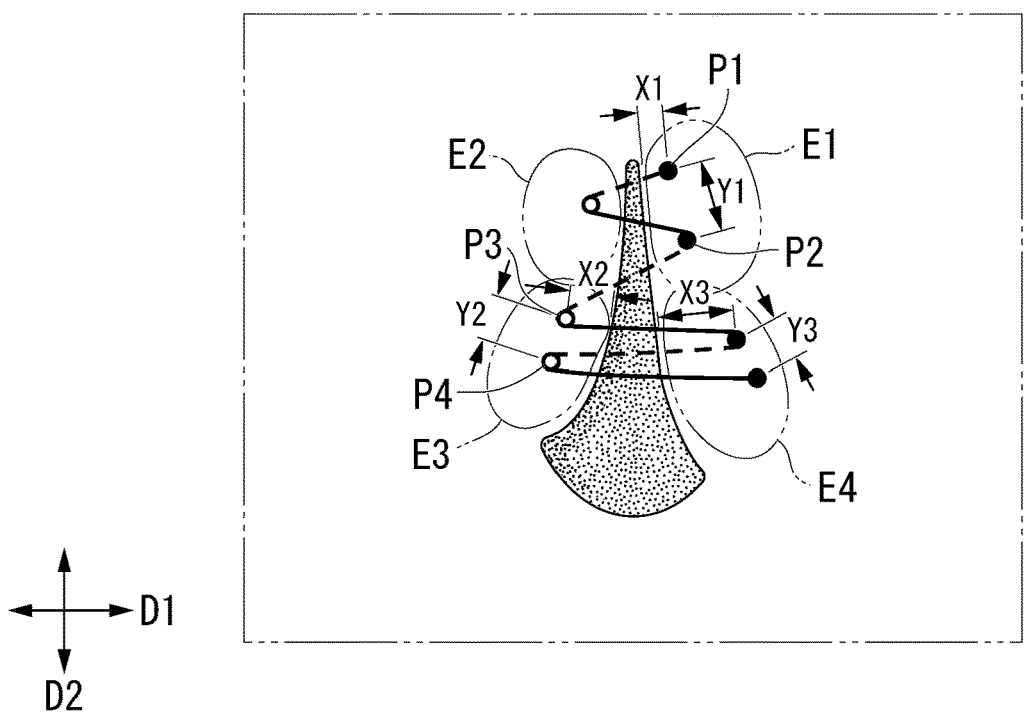
FIG. 25 is a diagram showing another aspect of the wound closing method.

In the wound closing method according to the above embodiment, the shortest distance X2 is larger than the shortest distance X1. However, the mode of the wound closing method is not limited to this. FIG. 25 is a diagram showing another aspect of the wound closing method of another aspect. It is desirable that the shortest distance X3 from the position on the mucosal surface through which the suture thread S is passed through the fourth edge portion E4 to the wound W also be larger than the shortest distance X1 at the first edge portion E1. Even when the force for separating the fourth edge portion E4 is large, the suture thread S does not easily come off from the fourth edge portion E4.

Figure 26:
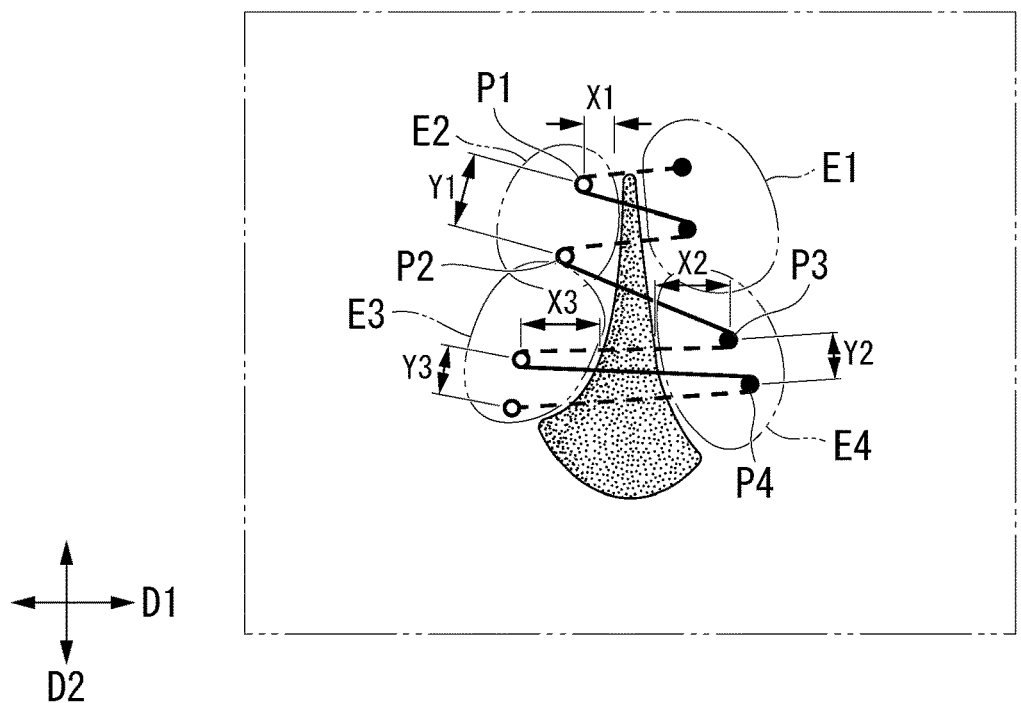
FIG. 26 is a diagram showing another aspect of the wound closing method.

In the wound closing method according to the above embodiment, the first position P1 and the second position P2 are arranged at the first edge portion E1, and the third position P3 and the fourth position P4 are arranged at the third edge portion E3. However, the mode of the wound closing method is not limited to this. FIG. 26 is a diagram showing another aspect of the wound closing method of another aspect. In the wound closing method shown in FIG. 26, the first step includes: step A of passing the suture thread S through the first position P1 on the mucosal surface of the second edge portion E2; step B of passing the suture thread S through the first edge portion E1; the first suturing step of pulling the suture thread S; and step C of passing the suture thread S through a second position P2 away from the first position P1 on the mucosal surface of the second edge portion E2. The second step includes: step D of passing the suture thread S through the third position P3 on the mucosal surface of the fourth edge portion E4; step E of passing the suture thread S through the third edge portion E3; step F of passing the suture thread S through the fourth position P4 away from the third position P3 on the mucosal surface of the fourth edge portion E4; and the second stitching step of pulling the suture thread S. Even in the wound closing method shown in FIG. 26, the shortest distance X2 is larger than the shortest distance X1. The second position P2 is not essential, and the suture thread S may be passed through the third position P3 of the fourth edge portion after the suture thread S is passed through the first position P1.

Further, in the modified example shown in FIG. 26, it is desirable that the shortest distance X3 from the position on the mucosal surface through which the suture thread S is passed through the third edge portion E3 to the wound W also be larger than the shortest distance X1 at the second edge portion E2. Even when the force for separating the third edge portion E3 is large, the suture thread S does not easily come off from the third edge portion E3.

In the above embodiment, the distance from the position through which the suture thread S is passed to the wound W (virtual surface V) is exemplified using the first position P1 and the third position P3. However, the distance from the position where the suture thread S is passed to the wound W (virtual surface V) is not limited to this. The distance from the position where the suture thread S is passed on the third edge portion E3 or the fourth edge portion E4 to the wound W (virtual surface V) should be larger than the distance from the position where the suture thread S is passed on the first edge portion E1 or the second edge portion E2 to the wound W (virtual surface V). This is because the suture thread S does not easily come off from the third edge portion E3 and the fourth edge portion E4.

Figure 27:
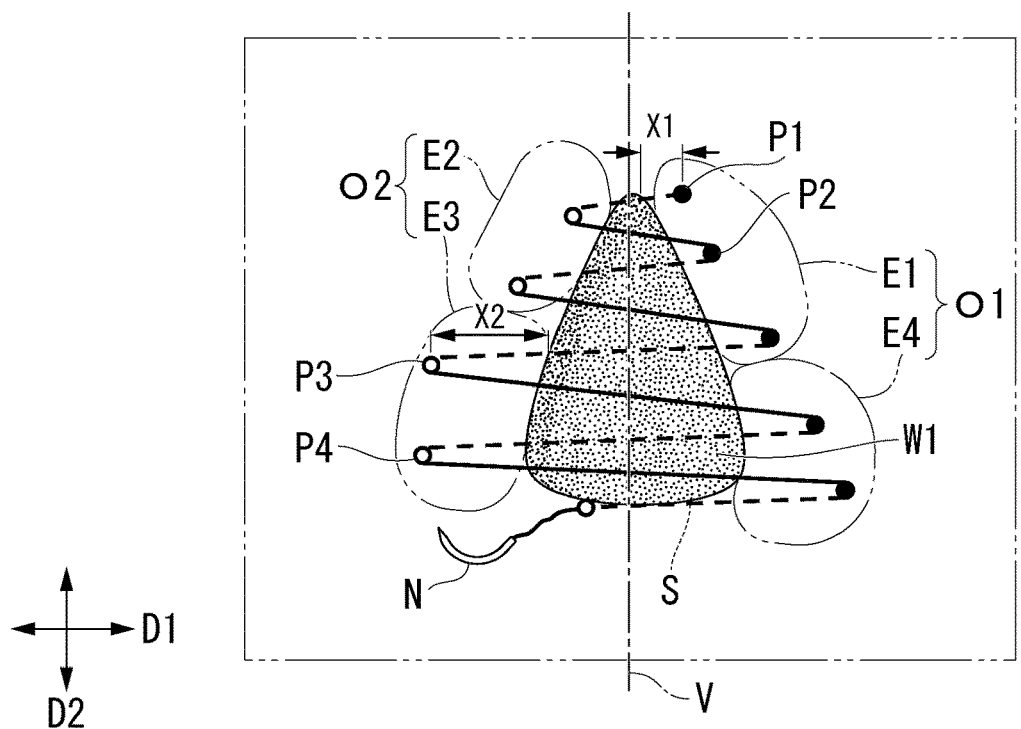
FIG. 27 is a diagram showing a modified example of the wound W.

In the above embodiment, the peripheral edge of the wound W is composed of the first facing edge portion (first edge portion E1, fourth edge portion E4, fifth edge portion E5) and the second facing edge portion O2 (second edge portion E2, third edge portion E3, sixth edge portion E6). However, the aspect of the wound W is not limited to this. FIG. 27 is a diagram showing a wound W1 which is a modified example of the wound W. The peripheral edge of the wound W1 is composed of the first facing edge portion O1 (first edge portion E1, fourth edge portion E4) and the second facing edge portion O2 (second edge portion E2, third edge portion E3). In this case, the wound closing method performs the first step and the second step in order. The third step is unnecessary because there are no fifth edge portion E5 and sixth edge portion E6.

Figure 28:
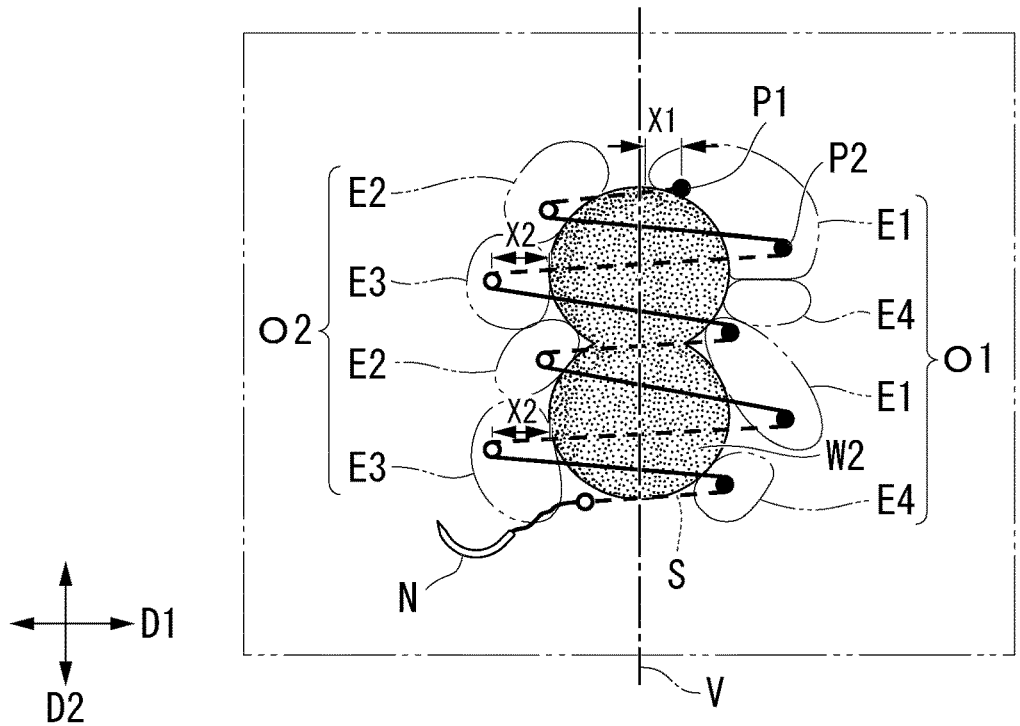
FIG. 28 is a diagram showing another modified example of the wound W.

FIG. 28 is a diagram showing a wound W2 which is a modified example of the wound W. The peripheral edge of the wound W2 is composed of the first facing edge portion O1 (first edge portion E1, fourth edge portion E4, first edge portion E1, fourth edge portion E4) and the second facing edge portion O2 (second edge portion E2, third edge portion E3, second edge portion E2, third edge portion E3). In this case, in the wound closing method, the first step and the second step are performed, and then the first step and the second step are performed again in order.

The method for closing the wound according to another exemplary embodiment will be described with reference to FIG. 29. In the following description, the same reference numerals will be given to the configurations common to those already described, and duplicate description will be omitted.

In the wound closing method according to the present embodiment, the shortest distance X2 does not necessarily have to be larger than the shortest distance X1 as compared with the wound closing method of the above embodiment. On the other hand, in the wound closing method according to the present embodiment, the second interval Y2 is smaller than the first interval Y1.

Figure 29:
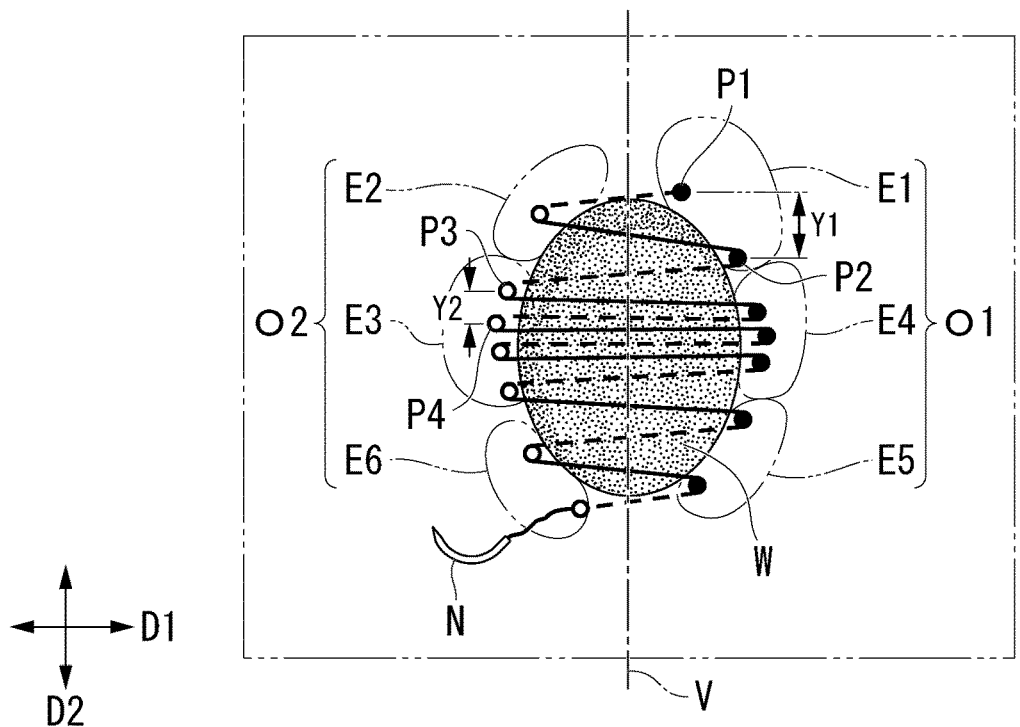
FIG. 29 is a diagram showing the suture thread passed through the wound by the wound closing method according to an exemplary embodiment.

FIG. 29 is a diagram showing a suture thread S passed through the wound W by the wound closing method according to the present embodiment. The suture thread S shown in FIG. 24 is not sutured. The first interval Y1 (see FIG. 15) is the interval between the first position P1 and the second position P2. The second interval Y2 (see FIG. 22) is the interval between the third position P3 and the fourth position P4.

The distance between the edge-ends of the edges facing each other on the peripheral edge of the wound W is the maximum between the edge-end T3 of the third edge portion E3 and the edge-end T4 of the fourth edge portion E4. Therefore, the force that causes the third edge portion E3 and the fourth edge portion E4 to be separated from each other is greatest at the peripheral edge of the wound W. However, since the second interval Y2 is smaller than the first interval Y1, the interval at the position where the suture thread S is passed through the third edge portion E3 in the depth direction D2 (direction along the virtual surface V) of the wound W can be reduced. As a result, even when the force for separating the third edge portion E3 is large, the force acting on the third edge portion E3 and the suture thread S can be dispersed.

According to the wound closing method according to the present embodiment, even a large wound W that cannot be closed by a clip can be suitably closed. The larger the defect of the wound W, the stronger the force to separate the first facing edge portion O1 and the second facing edge portion O2 after closing. According to the wound closing method according to the present embodiment, by reducing the distance between the positions where the suture thread S is passed through the third edge portion E3 where the force to be separated is the largest, the force acting on the third edge portion E3 and the suture thread S can be dispersed. As a result, the wound closing method according to the present embodiment can suitably close even a large wound W.

Although this embodiment has been described in detail with reference to the drawings, the specific configuration is not limited to this embodiment, and includes design changes and the like within a range that does not deviate from the gist of the present disclosure. In addition, the components shown in the above-described embodiments and modifications can be appropriately combined and configured.

In the wound closing method according to the above embodiment, the second interval Y2 is smaller than the first interval Y1. However, the mode of the wound closing method is not limited to this. In another aspect of the wound closure method shown in FIG. 25, it is desirable that the distance Y3 between the two positions on the mucosal surface through which the suture thread S is passed through the fourth edge portion E4 also be smaller than the first distance Y1 at the first edge portion E1. Even when the force for separating the fourth edge portion E4 is large, the force acting on the fourth edge portion E4 and the suture thread S can be dispersed.

In the wound closing method according to the above embodiment, the first position P1 and the second position P2 are arranged at the first edge portion E1, and the third position P3 and the fourth position P4 are arranged at the third edge portion E3. However, the mode of the wound closing method is not limited to this. In another aspect of the wound closure method shown in FIG. 26, the first step includes: step A of passing the suture thread S through the first position P1 on the mucosal surface of the second edge portion E2; step B of passing the suture thread S through the first edge portion E1; the first suturing step of pulling the suture thread S; and step C of passing the suture thread S through the second position P2 away from the first position P1 on the mucosal surface of the second edge portion E2. The second step includes: step D of passing the suture thread S through the third position P3 on the mucosal surface of the fourth edge portion E4; step E of passing the suture thread S through the third edge portion E3; step F of passing the suture thread S through the fourth position P4 away from the third position P3 on the mucosal surface of the fourth edge portion E4; and the second suturing step of pulling the suture thread S. Also, in the wound closing method shown in FIG. 26, the second interval Y2 is smaller than the first interval Y1.

Further, in the modified example shown in FIG. 26, it is desirable that the distance Y3 between the two positions on the mucosal surface through which the suture thread S is passed through the third edge portion E3 also be smaller than the first gap Y1 at the second edge portion E2. Even when the force that separates the third edge portion E3 is large, the force acting on the third edge portion E3 and the suture thread S can be dispersed.

In the above embodiment, the distance between the positions where the suture thread S is passed through the edge portion in the depth direction D2 (the direction along the virtual surface V) is exemplified by using the first distance Y1 and the second distance Y2. However, the distance between the positions where the suture thread S is passed through the edge in the depth direction D2 (direction along the virtual surface V) is not limited to this. It is desirable that the distance between the positions where the suture thread S is passed through the edge in the third edge portion E3 or the fourth edge portion E4 be smaller than the distance between the positions where the suture thread S is passed through the edge in the first edge portion E1 or the second edge portion E2. This is because the force acting on the third edge portion E3 and the fourth edge portion E4 and the suture thread S can be dispersed.

Figure 30:
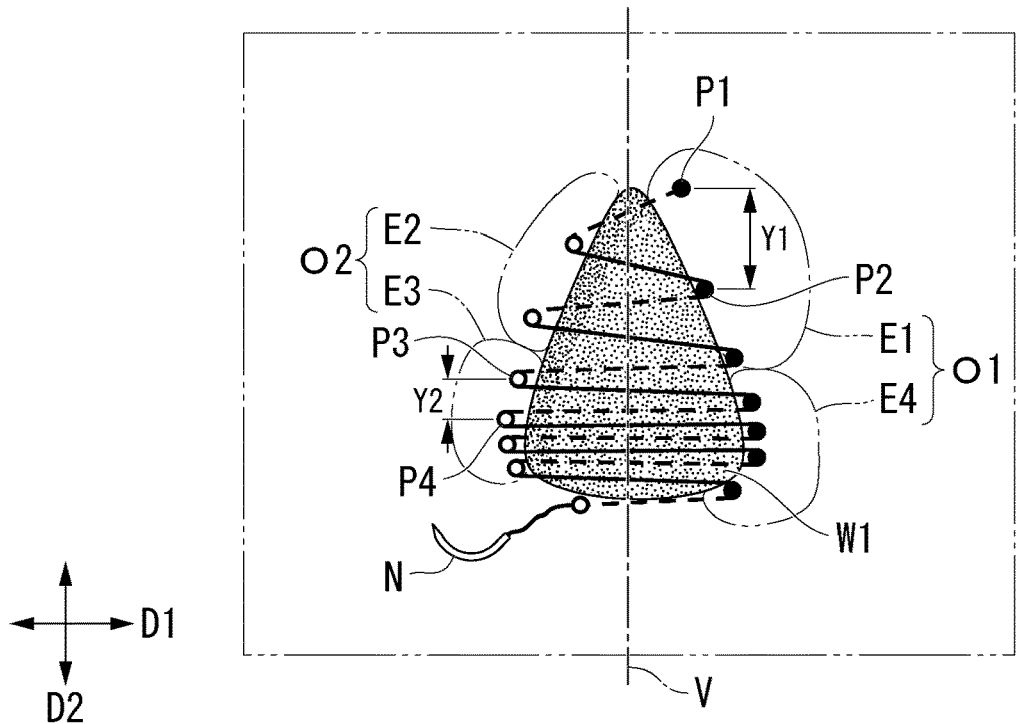
FIG. 30 is a diagram showing a modified example of the wound W.

In the above embodiment, the peripheral edge of the wound W is composed of the first facing edge portion O1 (first edge portion E1, fourth edge portion E4, fifth edge portion E5) and the second facing edge portion O2 (second edge portion E2, third edge portion E3, sixth edge portion E6). However, the aspect of the wound W is not limited to this. FIG. 30 is a diagram showing a wound W1 which is a modified example of the wound W. In the wound closing method, the first step and the second step are performed in order. The third step is unnecessary because there are no fifth edge portion E5 and sixth edge portion E6.

Figure 31:
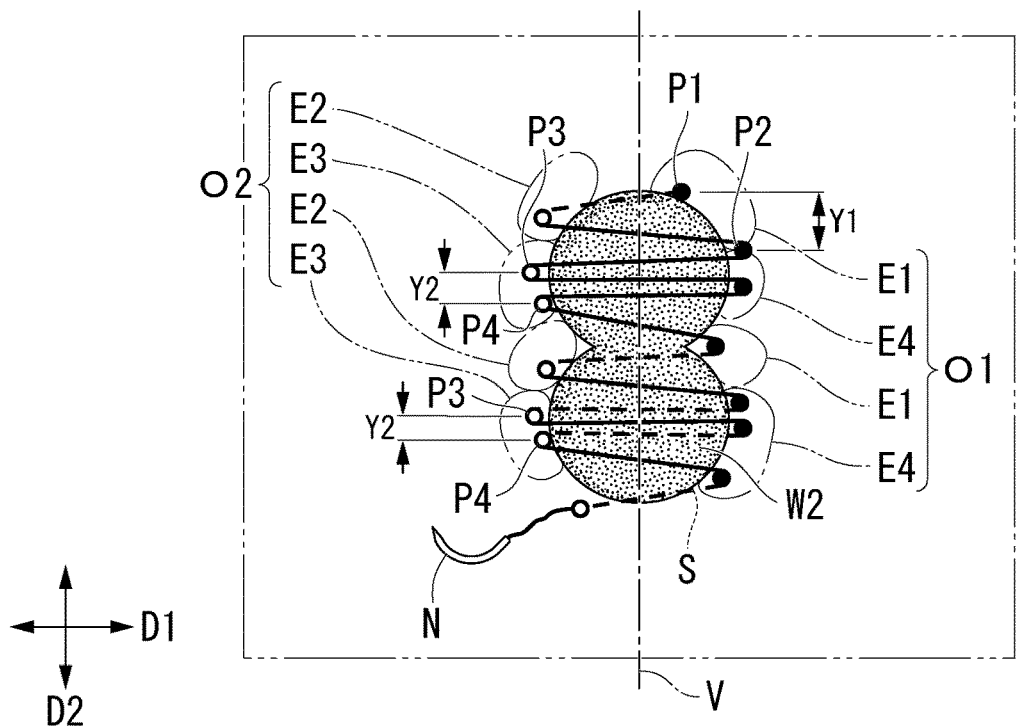
FIG. 31 is a diagram showing another modified example of the wound W.

FIG. 31 is a diagram showing a wound W2 which is a modified example of the wound W. In this case, in the wound closing method, the first step and the second step are followed by the first step and the second step in order.

The wound closing method according to another exemplary embodiment will be described with reference to FIGS. 32 to 33. In the following description, the same reference numerals will be given to the configurations common to those already described, and duplicate description will be omitted.

The wound closure method according to the present embodiment further has a reinforcement step after the third step as compared with the wound closure method of the above embodiment described with respect to FIGS. 1 to 24. Further, in the wound closing method according to the present embodiment, the shortest distance X2 does not necessarily have to be larger than the shortest distance X1 as compared with the wound closing method of the above embodiment (FIGS. 1 to 24).

Figure 32:
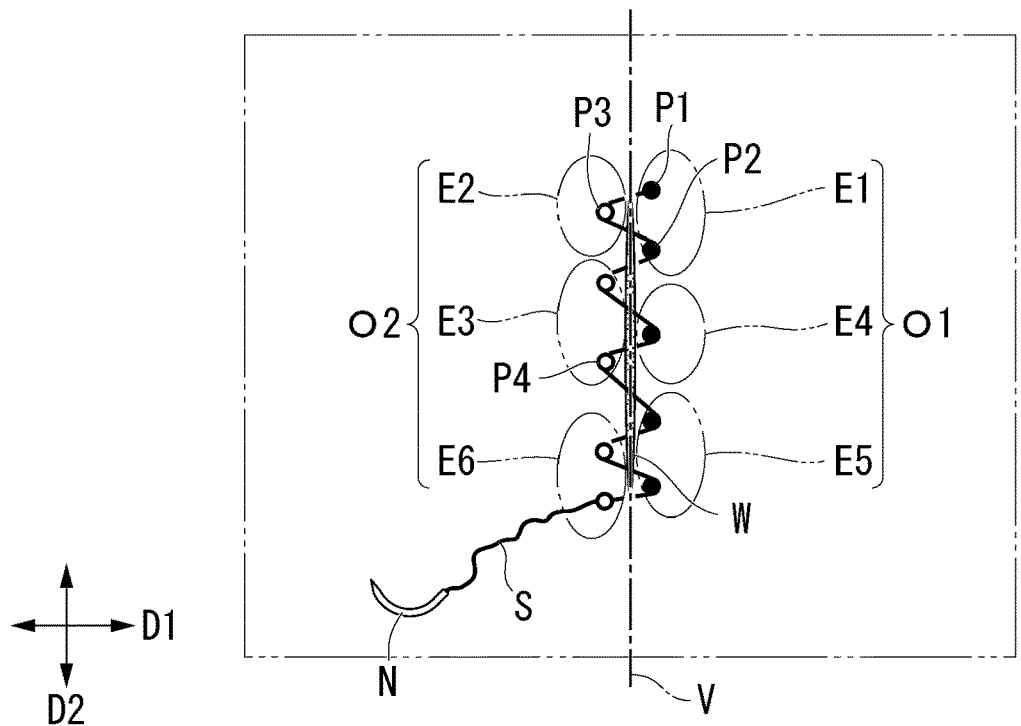
FIG. 32 is a diagram showing the wound after a third step in the wound closing method.

FIG. 32 is a diagram showing the wound W after the third step. The suture thread S shown in FIG. 32 is sutured. In the wound closing method according to the present embodiment, the reinforcement step is performed after the third step.

[Reinforcement Step]

Figure 33:
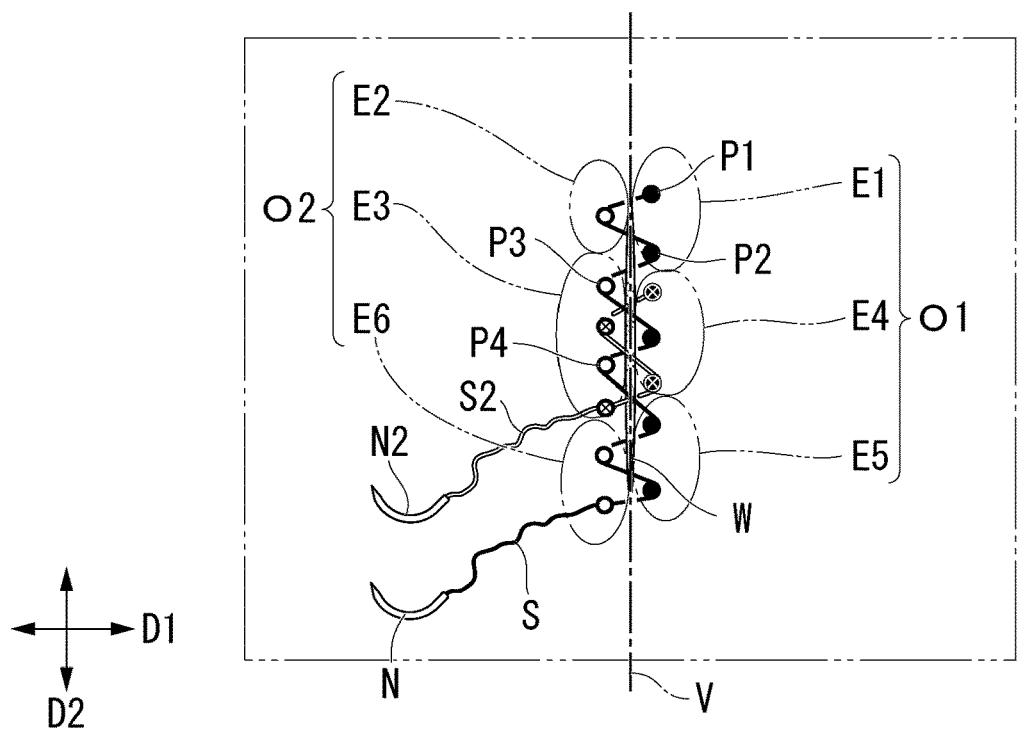
FIG. 33 is a diagram showing a reinforcement step.

FIG. 33 is a diagram showing the reinforcement step.

In the reinforcement step, by using the second suture needle N2 to which the second suture thread S2 different from the suture thread S is attached, the surgeon passes the second suture thread S2 through the third edge portion E3 and the fourth edge portion E4 in the same manner as in the second step. The position where the second suture thread S2 is passed through the third edge portion E3 by the reinforcement step is between the positions where the suture thread S is passed through the third edge portion E3. Further, the position where the second suture thread S2 is passed through the fourth edge portion E4 by the reinforcement step is between the positions where the suture thread S is passed through the fourth edge portion E4. As a result, the third edge portion E3 and the fourth edge portion E4 are connected by the second suture thread S2 alternately with the suture thread S.

At the third edge portion E3 or the fourth edge portion E4, the distance between the positions where the suture threads (suture thread S and the second suture thread S2) are passed through the edge portion becomes small. The force acting on the third edge portion E3 and the fourth edge portion E4 and the suture thread (suture thread S and second suture thread S2) can be dispersed.

According to the wound closing method according to the present embodiment, even a large wound W that cannot be closed by a clip can be suitably closed. The larger the defect of the wound W, the stronger the force to separate the first facing edge portion O1 and the second facing edge portion O2 after closing. According to the wound closing method according to the present embodiment, by reducing the interval between the positions where the suture threads (suture thread S and the second suture thread S) are passed through the third edge portion E3 and the fourth edge portion E4 where the force to be separated is the largest, the force acting on the third edge portion E3 and the fourth edge portion E4 and the suture thread (suture thread S and the second suture thread S) can be dispersed. As a result, the wound closing method according to the present embodiment can suitably close even a large wound W.

Although this embodiment has been described in detail with reference to the drawings, the specific configuration is not limited to this embodiment, and includes design changes and the like within a range that does not deviate from the gist of the present disclosure. In addition, the components shown in the above-described embodiments and modifications can be appropriately combined and configured.

Figure 34:
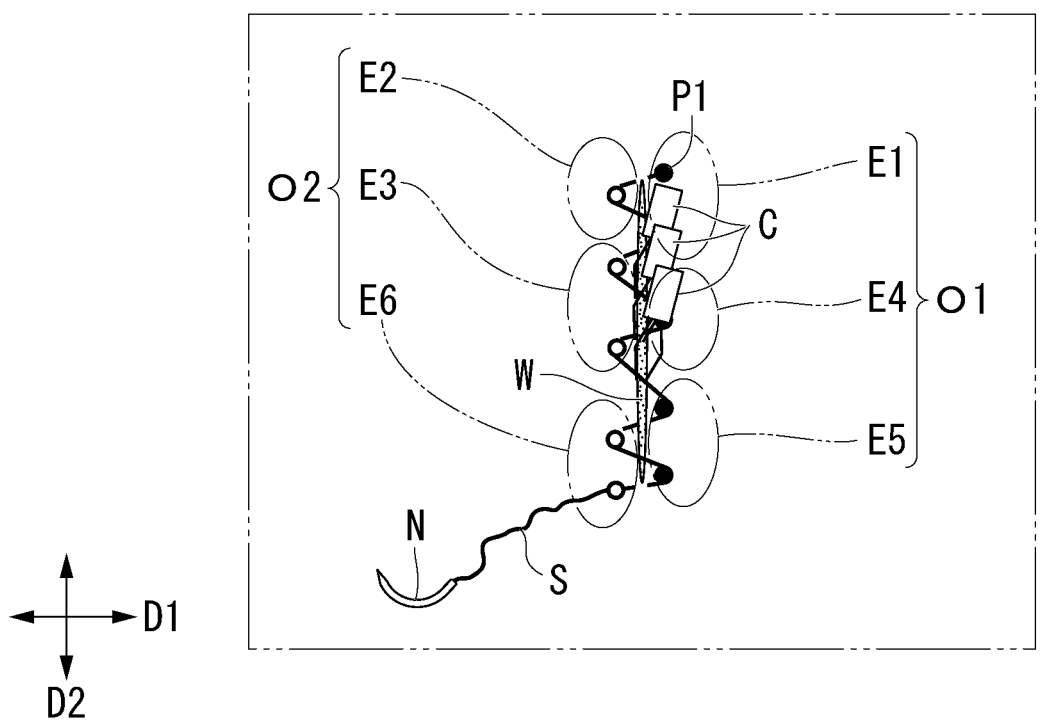
FIG. 34 is a diagram showing a modified example of the reinforcement step.

In the above embodiment, the reinforcement step is performed by the second suture thread S2 and the second suture needle N2. However, the correspondence of the reinforcement step is not limited to this. FIG. 34 is a diagram showing a modified example of the reinforcement step. The reinforcement step may be performed by sandwiching the third edge portion E3 and the fourth edge portion E4 with clips C. The force acting on the third edge portion E3 and the fourth edge portion E4 can be dispersed by the suture thread S and the clip C.

What is claimed is:

1. A method for closing a wound in a tubular organ, comprising:
   a step of suturing edges at opposing positions across the wound using a first device; and
   a step of suturing edges where a force to separate the wound acts greatest using a second device different from the first device.
2. The method according to claim 1, wherein
   a periphery of the wound includes a first edge, a second edge at a position opposite to the first edge across the wound, a third edge at a position adjacent to the second edge, and a fourth edge at a position opposite to the third edge across the wound,
   a distance between edges of the wound is largest between the third edge and the fourth edge,
   a distance between the first edge and the second edge is smaller than a distance between the third edge and the fourth edge,
   the step of suturing edges using the first device includes a first step of connecting the first edge and the second edge with the first device, and a second step of connecting the third edge and the fourth edge with the first device, and
   the step of suturing edges using the second device includes a reinforcing step of connecting the third edge and the fourth edge with the second device.
3. The method according to claim 2, wherein
   the second device is a clip, and
   the reinforcing step includes connecting the third edge and the fourth edge with the clip.
4. The method according to claim 3, wherein
   the first device is a suture thread,
   the first step includes connecting the first edge and the second edge with the suture thread, and
   the second step includes connecting the third edge and the fourth edge with the suture thread.
5. The method according to claim 4, wherein
   the suture thread is connected to a suture needle held by a needle holder protruding from a distal end of an endoscope, and
   the connecting of the first edge and the second edge with the suture thread includes penetrating a tissue surrounding the wound with the suture needle held by the needle holder protruding from the distal end of the endoscope.
6. The method according to claim 2, wherein
   the first device is a suture thread,
   the second device is a second suture thread,
   the first step includes connecting the first edge and the second edge with the suture thread,
   the second step includes connecting the third edge and the fourth edge with the suture thread, and
   the reinforcing step includes connecting the second suture threads alternately with the suture threads extending between the third edge and the fourth edge.
7. The method according to claim 5, wherein
   the second suture thread is connected to a suture needle held by a needle holder protruding from a distal end of an endoscope, and
   the connecting of the first edge and the second edge with the second suture thread includes penetrating a tissue surrounding the wound with the suture needle held by the needle holder protruding from the distal end of the endoscope.

* * * * *